(12) United States Patent
Song et al.

(10) Patent No.: US 9,995,749 B2
(45) Date of Patent: Jun. 12, 2018

(54) METHOD FOR DETECTING A TARGET ANALYTE

(71) Applicant: Agency for Science, Technology and Research, Singapore (SG)

(72) Inventors: Hong Yan Song, Singapore (SG); Ten It Wong, Singapore (SG); Anton Valentinovich Sadovoy, Singapore (SG); Xiaodong Zhou, Singapore (SG); Ping Bai, Singapore (SG); Lin Wu, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days. days.

(21) Appl. No.: 14/613,649

(22) Filed: Feb. 4, 2015

(65) Prior Publication Data

US 2015/0219643 A1 Aug. 6, 2015

(30) Foreign Application Priority Data

Feb. 4, 2014 (SG) .............................. 2014008098

(51) Int. Cl.
G01N 33/58 (2006.01)
G01N 33/553 (2006.01)
G01N 21/64 (2006.01)

(52) U.S. Cl.
CPC ......... *G01N 33/582* (2013.01); *G01N 21/648* (2013.01); *G01N 33/553* (2013.01); *G01N 33/588* (2013.01)

(58) Field of Classification Search
CPC ... G01N 21/648; G01N 33/553; G01N 33/588
See application file for complete search history.

(56) References Cited

U.S. PATENT DOCUMENTS

| | | | | |
|---|---|---|---|---|
| 2002/0182632 A1* | 12/2002 | Anderson | ............ | B82Y 15/00 435/7.1 |
| 2009/0073434 A1* | 3/2009 | Kim | .................. | G01J 3/0259 356/317 |
| 2012/0189700 A1* | 7/2012 | Aguilar | ............... | A61K 39/015 424/489 |

OTHER PUBLICATIONS

Malic et al., Designed Biointerface Using Near-Infrared Quantum Dots for Ultrasensitive Surface Plasmon Resonance Imaging Biosensors, Anal. Chem. 2011, 83, 5222-5229.*
Bedford et al., Surface Plasmon Resonance Biosensors Incorporating Gold Nanoparticles, Macromol. Biosci. 2012, 12, 724-739.*
Li et al., Electrochemiluminescence energy transfer-promoted ultrasensitive immunoassay using near-infrared-emitting CdSeTe/CdS/ZnS quantum dots and gold nanorods, Scientific Reports 3:1529, 1-10, Mar. 25, 2013.*

* cited by examiner

*Primary Examiner* — Andrea S Grossman
(74) *Attorney, Agent, or Firm* — Schwegman Lundberg & Woessner, P.A.

(57) ABSTRACT

There is method for detecting the presence or absence of a target analyte in a sample comprising the steps of: allowing an inorganic fluorescent particle to conjugate with a detection biomolecule that is bound to said target analyte, if present in said sample, said target analyte additionally being bound by a capture biomolecule immobilized on or within a nanostructure; and detecting the fluorescence emitted by said inorganic fluorescent particle, said nanostructure being capable of generating a surface plasmon resonance effect when excited by a light source to substantially increase the fluorescence emitted by said inorganic fluorescent particle, wherein the detected fluorescence indicates the presence of said target analyte in said sample.

20 Claims, 14 Drawing Sheets

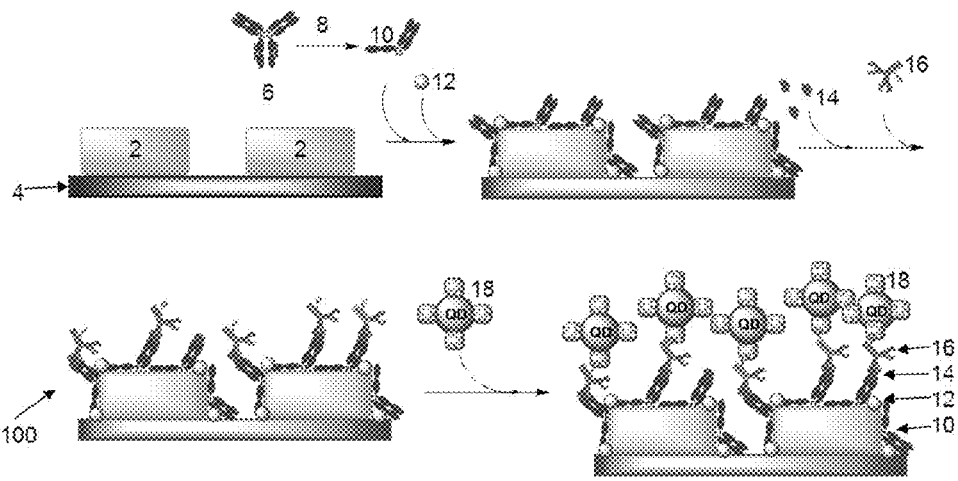
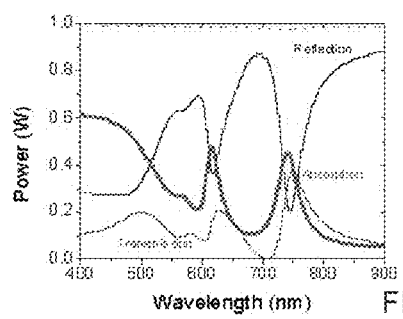
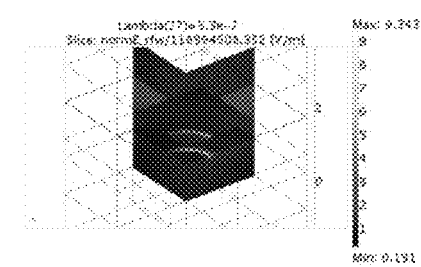
FIG. 2A
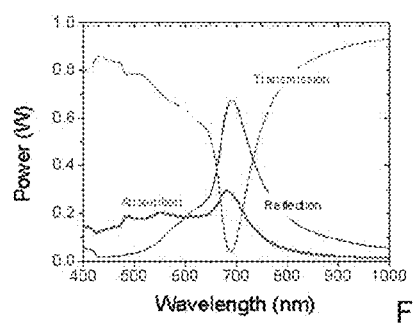
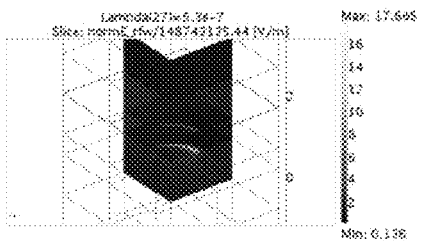
FIG. 2B

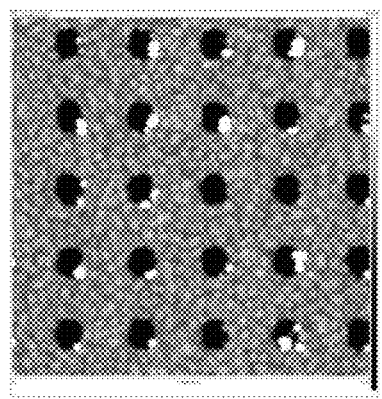
FIG. 5A
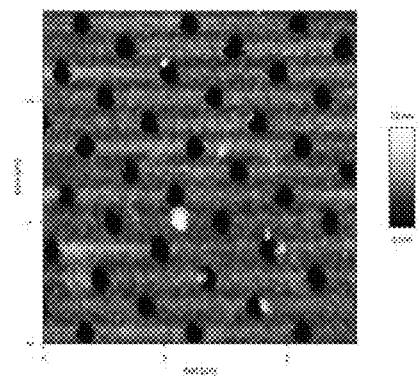
FIG. 5B
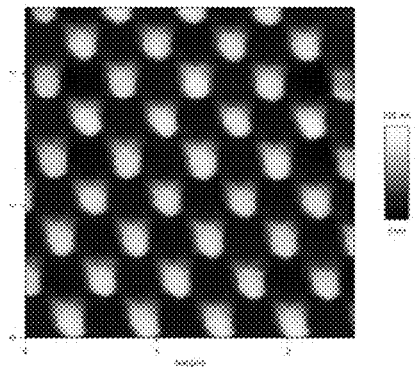
FIB. 5C
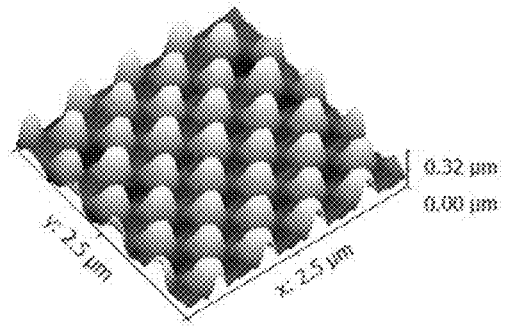
FIG. 5D

METHOD FOR DETECTING A TARGET ANALYTE

CLAIM OF PRIORITY

This application claims the benefit of priority of Singapore Patent Application Serial No. 2014008098, filed on Feb. 4, 2014, the benefit of priority of which is claimed hereby, and which is incorporated by reference herein in its entirety.

TECHNICAL FIELD

The present invention generally relates to a method for detecting the presence or absence of a target analyte in a sample. The present invention also relates to a kit for detecting the presence or absence of a target analyte in a sample.

BACKGROUND ART

In the field of medical diagnosis, many biomarkers of interest are present in body samples at low concentrations and require label amplifications such as radioluminescence, photoluminescence, gold or polymer microparticles or nanoparticles for detection. With the current medical diagnostic trends of ensuring that most of the population are covered by health screening, reducing medical costs, serving the healthcare needs of patients and saving lives in-time, point-of-care systems for medical diagnostics are of great interest. A point-of-care system usually has a disposable microfluidic chip to capture the analytes for on-site detections. In such a system, if fluorescence is used as the detection mechanism for a sandwich assay in which a target antigen is bound between a capture antibody immobilized on a substrate and a detection antibody that is conjugated with a fluorescence dye, the fluorescence signal emitted from the fluorescence dye in such a 2-dimensional substrate is much weaker than the 3-dimensional fluorescence dye emission in homogeneous liquid. Nevertheless, 2-dimensional substrates are attractive candidates for a fully automated point-of-care system as the analytes can be captured on the substrate and detected easily.

In order to compensate the sensitivity loss of the signal due to the 2-dimensional substrate, a well-known method is to utilize surface plasmon resonance (SPR) generated by a gold film to enhance the fluorescence dyes. When a gold film is coated on the glass substrate, high sensitivity enhancement can be achieved by combining a Kretschmann configuration, where SPR excited by the transverse magnetic mode of light on the gold film will enhance the fluorescence signal, and a biomarker can be detected at a limit of detection as low as 2 pg/ml with a photomultiplier tube (PMT) through a dextran matrix on the SPR chip. However, the Kretschmann configuration is a complicated system, not readily portable and expensive due to the need for the photomultiplier.

An alternative to this technology is to utilize the localized surface plasmon resonance (LSPR) generated by gold nanostructures fabricated on glass chip, where the fluorescence can theoretically be enhanced up to 1300 times on the plasmonic hotspots, and at an average of 10-200 times. LSPR can excite the fluorescence dyes at any angle such as normal light incidence, where the light transmission mode or reflection mode can be employed to form a very simple point-of-care system. However, in these experiments, the plasmonic enhancement of the fluorescence dye emission is only feasible to achieve 10 to 100 times sensitivity enhancement, and they require a sensitive photodetector or PMT, or a confocal microscope for detection. The inventors have found that such a system cannot be detected using a dark-field microscope and that there are difficulties in detecting the fluorescence label of the LSPR at a low clinical required sensitivity.

Besides the above mentioned weak signal, organic fluorescence dyes are also disadvantageous due to the small gap between their excitation wavelength and emission wavelength, in which the gap is just 15 to 30 nm. Since the light intensity of the fluorescence emission is much weaker than the excitation, in order to reduce the large background noise due to the crosstalk of the excitation, either a dark-field condenser or a high quality optical filter must be used, both of which are expensive and inconvenient for building up a point-of-care system.

There is a need to provide a method for detecting a target analyte that overcomes, or at least ameliorates, one or more of the disadvantages described above.

SUMMARY OF INVENTION

According to a first aspect, there is provided a method for detecting the presence or absence of a target analyte in a sample comprising the steps of allowing an inorganic fluorescent particle to conjugate with a detection biomolecule that is bound to said target analyte, if present in said sample, said target analyte additionally being bound by a capture biomolecule immobilized on or within a nanostructure; and detecting the fluorescence emitted by said inorganic fluorescent particle, said nanostructure being capable of generating a surface plasmon resonance effect when excited by a light source to substantially increase the fluorescence emitted by said inorganic fluorescent particle, wherein the detected fluorescence indicates the presence of said target analyte in said sample.

The present inventors have shown for the first time that notwithstanding the larger size of the inorganic fluorescent particles (as compared to the smaller organic fluorescent dyes, which can cause the (localized) surface plasmon resonance field to decay exponentially as the height of the inorganic fluorescent particles increases), inorganic fluorescent particles such as quantum dots can be used in detection methods and kits that utilize (localized) surface plasmon resonance nanostructures. In order to circumvent the larger size of the inorganic fluorescent particles and difficulty in positioning the larger inorganic fluorescent particles within the plasmonic field, the inventors have found that, in one embodiment, by reducing the size of the biomolecule(s) used in the present method such as by end-on immobilization of the fragmented biomolecule(s) on the surface of the nanostructure, the inorganic fluorescent particles can be drawn closer to areas with a strong (localized) surface plasmon resonance effect. By this additionally, the surface density of the active parts of the capture biomolecule may also be increased, allowing for more interaction and capture of the target analyte. In another embodiment, the detection biomolecule may be fragmented.

It is to be noted that in another embodiment, the capture biomolecule may not be fragmented and may be a complete biomolecule, as long as the inorganic fluorescent particle can be placed appropriately in the plasmonic field and without any substantial decay in the surface plasmon resonance field as the height of the assay (made up of the capture biomolecule/target analyte/detection biomolecule/inorganic fluorescent particle) increases.

Advantageously, due to the enhancement of the quantum dot fluorescent by the surface plasmon resonance of the nanostructures, the intensity of the quantum dot fluorescence and/or the energy gap between the excitation light and emission signal can be significantly increased by about 10 to about 1000 times (depending on the assay and nanostructure design) as compared to a assay/biochip where nanostructures are absent. This may aid in the construction of a transmission and imaging based inexpensive point-of-care system.

Due to the surface functionalization of the (localized) surface plasmon resonance chip with the quantum dot sandwich bioassay of the present disclosure, brighter photoluminescent signal, longer life-time, more stable signal, and/or higher sensitivity can be achieved in the present disclosure. The localized surface plasmon resonance-quantum dot bioassay developed in this invention has large energy gap between the quantum dot excitation and emission, which will ease the separation of the relatively weak photoluminescence from the strong excitation and increase the signal-to-noise ratio. Hence, the inability associated with conventional point-of-care systems on detecting low photoluminescence of organic fluorescent dyes may be overcome by the present disclosure with the use of quantum dots on localized surface plasmon resonance chips, the present disclosure being the first to show that quantum dots emissions can be used for analyte detections on a biochip having surface plasmon resonance or localized surface plasmon resonance (or co-excitation thereof).

There may be provided a system comprising a nanostructure with an immobilized capture biomolecule thereon, the capture biomolecule bound to a target analyte that may be present in a sample, the target analyte in turn bound to a detection biomolecule that is conjugated to an inorganic fluorescent particle, the nanostructure being capable of generating a surface plasmon resonance effect when excited by a light source to substantially increase the fluorescence emitted by the inorganic fluorescent particle, wherein the detected fluorescence indicates the presence of the target analyte in the sample. The system may be a bioassay.

The bioassay of the present disclosure can be used to detect antigens having a concentration as low as 100 pg/ml using a simple charge-coupled device (CCD) camera. On the other hand, for conventional bioassays that are based on organic fluorescent dyes, special and expensive detectors such as photomultiplier must be used. Hence, the bioassay of the present disclosure exhibits greater sensitivity improvement compared with bioassays using organic fluorescence dyes.

According to a second aspect, there is provided a kit for detecting the presence or absence of a target analyte in a sample comprising: a substrate having a nanostructure thereon for immobilizing a capture biomolecule on or within said nanostructure, said capture biomolecule being capable of binding specifically to said target analyte, if present in said sample; a detection biomolecule capable of binding specifically to said target analyte, if present in said sample; and an inorganic fluorescent particle capable of conjugating with said detection biomolecule to form a detection reagent, wherein upon excitation by a light source, said nanostructure is capable of generating a surface plasmon resonance effect to thereby enhance the fluorescence emitted by said detection reagent when bound to said target analyte, if present in said sample.

DEFINITIONS

The following words and terms used herein shall have the meaning indicated:

The term "target analyte", as used herein, refers to a substance to be detected that is capable of binding to a capture biomolecule and a detection biomolecule. Hence, the target analyte may have at least two different binding sites, one for binding with the capture biomolecule and the other for binding with the detection biomolecule. A target analyte may also be a substance to be detected for calibration purposes. Exemplary target analytes include, but are not limited to, nucleic acids, polynucleotides, drugs, hormones, proteins, enzymes, antibodies, carbohydrates, receptors, bacteria, cells, virus particles, spores, allergens and antigens.

The term "capture biomolecule", as used herein, refers to a biomolecule that is able to bind to the target analyte. The capture biomolecule may have a biological activity. It is to be noted that the term "capture biomolecule" may refers to a complete (or whole) biomolecule or parts or fragments of the complete (or whole) biomolecule, the complete biomolecule or parts or fragments thereof having binding site(s) that is(are) able to bind to the target analyte. The capture biomolecule may be an antibody, a protein, a nucleic acid. Where the capture biomolecule is a fragmented capture biomolecule, the term "fragmented capture antibody" refers to capture biomolecules that are a part or fragment of the complete (or whole) biomolecule, the fragmented capture biomolecule having a smaller size/shape/configuration as compared to its corresponding complete (or whole) biomolecule.

Where the complete biomolecule is a full-length antibody, the fragmented capture biomolecule may refer to fragments of the antibody that contain an antigen binding site(s) for binding to the target analyte (in this case, being an antigen). Examples of such antibody fragments encompassed within the term "fragmented capture biomolecule" include (i) a Fab' or Fab fragment, a monovalent fragment consisting of the $V_L$, $V_H$, $C_L$ and $C_H1$ domains; (ii) F(ab')$_2$ fragments, bivalent fragments comprising two Fab fragments linked by a disulfide bridge at the hinge region; (iii) a Fd fragment consisting essentially of the $V_H$ and $C_H1$ domains; (iv) a Fv fragment consisting essentially of the $V_L$ and $V_H$ domains of a single arm of an antibody, (v) a dAb fragment, which consists essentially of a $V_H$ domain and also called domain antibodies; (vi) camelid or nanobodies, (vii) an isolated complementarity determining region (CDR) and (viii) rIgG fragment, which refers to reduced IgG as a result of selectively reducing just the hinge-region disulfide bonds of IgG.

Where the complete biomolecule is a protein, the fragmented capture biomolecule may refer to a peptide, which consists of short chains of amino acids, having qualitative biological activity in common with the corresponding protein. Hence, here, the target analyte may be a protein, enzyme, hormone, drugs or nucleic acids.

Wherein the complete biomolecule is a nucleic acid (such as DNA or RNA), the fragmented capture biomolecule may refer to an oligonucleotide, which is a short, single-stranded nucleic acid from 2 to about 500 bases. The oligonucleotide may be a primer that contains sufficient base pairs for recognition and hybridisation with the complementary sequence on the target analyte, being another oligonucleotide or a nucleic acid in this case. The fragmented capture biomolecule, depending on its type, may be artificially synthesized or may be obtained from their corresponding complete biomolecule by cleaving or reduction using chemical or enzymes.

The term "detection biomolecule", as used herein, refers to a biomolecule that is able to bind to the target analyte, the binding site for the detection biomolecule being different from that for the capture biomolecule. The detection biomolecule may be a complete biomolecule or a fragment thereof. Where the detection biomolecule is a part or a fragment, the detection biomolecule may be termed as a "fragmented detection biomolecule". Hence, the detection biomolecule may be an antibody, a protein, a nucleic acid while the fragmented detection biomolecule may refer to an antibody fragment, a peptide or an oligonucleotide. The detection biomolecule or fragmented detection biomolecule may be chemically modified to contain a moiety that is capable of conjugating with an inorganic fluorescent particle. Hence, the detection biomolecule or fragmented detection biomolecule may be chemically modified with biotin for binding with avidin, streptavidin or neutravidin. Conversely, the detection biomolecule or fragmented detection biomolecule may be chemically modified with the avidin, streptavidin or neutravidin for conjugation with the biotinylated inorganic fluorescent particle.

The detection biomolecule or fragmented detection biomolecule may be pre-labelled with the inorganic fluorescent particle using covalent or non-covalent bio-conjugation methods, such as classical covalent methods (amine EDC/NHS coupling, aldehyde-amine coupling, thiol-maleimide coupling, epoxide-nucleophile coupling, and various glycoside coupling); ligation coupling (Staudinger ligation coupling, Huisgen 1,3 dipolar cycloaddition/"click" reaction, Diels-Alder cycloaddition); transition metal mediated chelation conjugation; and enzyme catalysed protein labelling. The term "detection reagent" thus refers to the detection biomolecule (or fragmented detection biomolecule) conjugated with the inorganic fluorescent particle.

The phrases "specifically binding", "binding specifically", "binding selectively" or "selectively binding", as used herein, refers to the abilities of the capture biomolecule and detection biomolecule (or respective fragments thereof) to bind to the target analyte or the ability of the detection biomolecule (or fragment thereof) to bind to the inorganic fluorescent particle.

The term "nanostructure", as used herein, refers to freestanding or isolated three dimensional structures that extend from the base of a substrate which have at least two dimensions that are less than about 1 μm, more typically 20 nm to 800 nm, or less than 100 nm. The nanostructure may be made from or covered with a film of metal that is able to generate a surface plasmon resonance or localized surface plasmon resonance effect (or both) when excited by a light source.

The term "Surface Plasmon Resonance" or SPR is to be interpreted to refer to a resonance condition when the tangential component of the wave vector of a light incident on a metallic layer matches to the wave vector of the surface plasmons. At this condition, energy is transferred from the incident light to the surface plasmons. This is indicated by a drop in the intensity of light reflected from the surface of the metallic layer. The resonance condition depends on the wavelength of the incident light, the frequency of the incident light, the refractive index of all materials used in the surface plasmon resonance device and the angle at which the light is incident on the reflective material layer.

The term "three dimensional" is to be interpreted broadly to include any structures, structural features, imprints or patterns that have both lateral variations (thickness) as well as variations with depth.

The term "inorganic fluorescent particle" is to be interpreted broadly to include any semiconductive or metallic nanoparticle that is capable of emitting a light signal. The inorganic fluorescent particle may be a quantum dot. The particle size of the quantum dot is typically about 1 nm to about 1000 nm, more typically less than about 2 nm to about 10 nm. The shape of the quantum dot is not limited and may be in the shape of a sphere, a rod, a wire, a pyramid, a cube, or other geometric or non-geometric shapes. The colour of the light emitted by the quantum dot depends on a number of factors that include the size and shape of the quantum dot. For example, a quantum dot with a larger particle size emits light with a lower energy as compared to a quantum dot made of the same material but with a smaller particle size.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of a method for detecting the presence or absence of a target analyte in a sample will now be disclosed.

The method may comprise the steps of allowing an inorganic fluorescent particle to conjugate with a detection biomolecule that is bound to the target analyte, if present in the sample, the target analyte additionally being bound by a capture biomolecule immobilized on or within a nanostructure; and detecting the fluorescence emitted by inorganic fluorescent particle, the nanostructure being capable of generating a surface plasmon resonance effect when excited by a light source to substantially increase the fluorescence emitted by inorganic fluorescent particle, wherein the detected fluorescence indicates the presence of said target analyte in said sample.

The method may further comprise, before the allowing step, the steps of providing a sample suspected of containing said target analyte to said immobilized capture biomolecule and allowing the target analyte to bind to the immobilized capture biomolecule, The target analyte that binds to the immobilized capture biomolecule is then captured by the immobilized capture biomolecule, forming a captured target analyte.

The method may further comprise, before the providing and allowing steps, the step of immobilizing the capture biomolecule on or within the nanostructure.

The method may be deemed to contain the following steps:
- providing a sample suspected of containing a target analyte to a capture biomolecule immobilized on or within a nanostructure;
- allowing the target analyte to bind to the immobilized capture biomolecule;
- binding a detection reagent to the target analyte; and
- detecting the fluorescence emitted by the bound detection reagent,
- wherein the nanostructure is capable of generating a surface plasmon resonance effect when excited by a light source to enhance the fluorescence emitted by the detection reagent, and wherein the presence of the fluorescence indicates the presence of the target analyte.

The method may also be deemed to contain the following steps:
- immobilizing a capture biomolecule on or within a nanostructure;
- providing a sample suspected of containing a target analyte to the immobilized capture biomolecule;
- allowing the target analyte to bind to the immobilized capture biomolecule;
- binding a detection reagent to the target analyte; and
- detecting the fluorescence emitted by the bound detection reagent,
- wherein the nanostructure is capable of generating a surface plasmon resonance effect when excited by a light source to enhance the fluorescence emitted by the detection reagent, and wherein the presence of the fluorescence indicates the presence of the target analyte.

The method may also be deemed to contain the following steps:
- cleaving a biomolecule into parts or fragments, each part or fragment forming a capture biomolecule;
- immobilizing the capture biomolecule on or within a nanostructure;
- providing a sample suspected of containing a target analyte to the immobilized capture biomolecule;
- allowing the target analyte to bind to the immobilized capture biomolecule;
- binding a detection reagent to the target analyte; and
- detecting the fluorescence emitted by the bound detection reagent,
- wherein the nanostructure is capable of generating a surface plasmon resonance effect when excited by a light source to enhance the fluorescence emitted by the detection reagent, and wherein the presence of the fluorescence indicates the presence of the target analyte.

A detection reagent may be formed from the inorganic fluorescent particle conjugated to the detection biomolecule (prepared as stated above). Hence, the method may additionally comprise the step of conjugating a detection biomolecule to the inorganic fluorescent particle to thereby form the detection reagent, the detection biomolecule comprising a moiety for conjugating with a corresponding substance on the inorganic fluorescent particle. The fluorescence is then detected from the conjugated inorganic fluorescent particle.

The disclosed method may be used to detect target analytes such as nucleic acids, polynucleotides, drugs, hormones, proteins, enzymes, antibodies, carbohydrates, receptors, bacteria, cells, virus particles, spores, allergens or antigens. The type of target analyte is not limited and can include any target analyte that an end-user may wish to identify, track or monitor in medical diagnosis, calibration of instruments or equipments, or for checking the efficacy of a treatment regime (such as over a period of time).

The target analyte may contain at least two binding sites for specifically binding with the capture biomolecule and the detection biomolecule. The type of capture biomolecule and detection biomolecule is then dependent on the target analyte. As an example, where the target analyte is an antigen, the capture biomolecule may be an antibody or fragment thereof and the detection biomolecule may be another antibody or fragment thereof. Where the target analyte is a protein, the capture biomolecule may be a protein or a part thereof (such as a peptide) and the detection biomolecule may be a protein or a part thereof (such as a peptide). Where the target analyte is a nucleic acid, the capture biomolecule may be an (single-stranded) nucleic acid or oligonucleotide that hybridises to a section of the target analyte and the detection biomolecule can be another (single-stranded) nucleic acid or oligonucleotide that is able to hybridise onto another section of the target analyte. It is also possible for the capture biomolecule to be an antibody fragment or peptide that is able to bind to the nucleic acid target analyte and the detection biomolecule can either be an antibody, protein or nucleic acid (or an antibody fragment, a peptide or an oligonucleotide). In one embodiment, the capture biomolecule may be a fragmented capture biomolecule while the detection biomolecule is a complete biomolecule. In another embodiment, the capture biomolecule may be a complete biomolecule while the detection biomolecule is a fragmented detection biomolecule. In yet another embodiment, the capture biomolecule may be a fragmented capture biomolecule while the detection biomolecule may be a fragmented detection biomolecule. In still another embodiment, the capture biomolecule may be a complete capture biomolecule while the detection biomolecule is another complete biomolecule (while keeping the inorganic fluorescent particle within the plasmon resonance field). Accordingly, depending on the type of target analyte to be detected, an end-user would know what capture biomolecule and detection biomolecule to be used.

The limit of detection (LOD) of the target analyte can be as low as 100 pg/ml. As target analytes may be present at very low concentrations in a body sample, the disclosed method may be advantageously used to easily and conveniently detect target analytes that cannot be detected easily with conventional bioassays. The disclosed method may not require the use of complicated or specialised equipment to detect target analytes of low concentration.

The method may allow for determining the concentration of the target analyte. This may be achieved by obtaining the light intensity emitted by the detection reagent (which may be normalised as required) that is bound to the target analyte of an unknown concentration. The light intensity may then be inserted into an equation which was obtained by charting the light intensities obtained with the same target analyte at a number of known concentrations. Hence, the method may be used to determine the concentration of a target analyte that may be below the detection limit of colorimetric assays, absorbance assays or gels (when compared to a quantitative standard).

The above configuration of the capture biomolecule/target analyte/detection reagent can be termed as a sandwich assay. To ensure that the inorganic fluorescent particle is within the (localised) surface plasmon resonance field of the nanostructure, the height of the capture biomolecule may be about 1 nm to about 300 nm, about 1 nm to about 20 nm, about 1 nm to about 5 nm, about 1 nm to about 10 nm, about 1 nm to about 15 nm, about 1 nm to about 50 nm, about 1 nm to about 75 nm, about 1 nm to about 100 nm, about 1 nm to about 125 nm, about 1 nm to about 150 nm, about 1 nm to about 175 nm, about 1 nm to about 200 nm, about 1 nm to about 225 nm, about 1 nm to about 250 nm, about 1 nm to about 275 nm, about 5 nm to about 300 nm, about 10 nm to about 300 nm, about 15 nm to about 300 nm, about 50 nm to about 300 nm, about 75 nm to about 300 nm, about 100 nm to about 300 nm, about 125 nm to about 300 nm, about 150 nm to about 300 nm, about 175 nm to about 300 nm, about 200 nm to about 300 nm, about 225 nm to about 300 nm, about 250 nm to about 300 nm, or about 275 nm to about 300 nm. In order to achieve this height, the capture biomolecule may be cleaved or reduced using a cleaving agent from its corresponding complete (or whole) biomolecule or may be artificially synthesized. The cleaving agent may be a chemical such as tris(2-carboxyethyl)phosphine, dithiothreitol or 2-mercaptoethanol or may be an enzyme such as a protease. The protease may be an endopeptidase such as but not limited to trypsin, chymotrypsin, elastase, thermolysin, pepsin, glutamyl endopeptidase, ficain, papain, bromelase, calpain, caspase, cathepsin B, chymopapain, etc. It is to be appreciated that the above are only examples of some cleaving agents and are not meant to be limited to just the above.

The capture biomolecule may be a fragmented capture biomolecule, The fragmented capture biomolecule may be an antibody fragment, the antibody fragment may be selected from the group consisting of F(ab')$_2$, Fab, Fab', Fd, Fv dAb, camelid, nanobody, isolated complementarity determining region, sFv, scFv and r IgG fragment.

The capture biomolecule may be functionalized with a chemical moiety for binding to the surface of the nanostructure. As an example, where the capture biomolecule is an antibody fragment, the antibody fragment may contain terminal thiol functional groups that are able to bind to the nanostructure (the nanostructure being gold nanostructure here).

The use of fragments or parts as capture biomolecule may also aid in exposing more binding sites for binding with the target analyte.

After immobilizing the capture biomolecule onto the nanostructure, a blocking agent may be added to block free immobilization sites on the nanostructure (or substrate supporting the nanostructure) that are not covered by the capture biomolecules. This may aid in preventing non-specific binding of the target analyte to the surfaces of the nanostructure and/or substrate. Blocking agents are typically used in bioassay and examples of which are bovine serum albumin, nonfat milk, casein, or poly(ethylene glycol). It is to be noted that the choice of blocking agent depends on the type of target analyte and the detection biomolecule used and an end-user would know what blocking agent to use.

As mentioned above, the type of detection biomolecule depends on the target analyte to be detected. The detection biomolecule may be chemically modified to contain a moiety that is capable of binding with a corresponding substance on the inorganic fluorescent particle. Hence, the detection biomolecule may be chemically modified with biotin for binding with avidin, streptavidin or neutravidin. Conversely, the detection biomolecule may be chemically modified with the avidin, streptavidin or neutravidin for conjugation with the biotinylated inorganic fluorescent particle. It is to be appreciated that conjugation between the detection biomolecule and the inorganic fluorescent particle is not limited to the affinity pair of avidin-biotin, and that other types of affinity/bio-conjugation pairs can be used as required and if suitable.

The detection biomolecule may have a height of about 0.1 nm to about 300 nm, about 1 nm to about 20 nm, about 1 nm to about 5 nm, about 1 nm to about 10 nm, about 1 nm to about 15 nm, about 1 nm to about 50 nm, about 1 nm to about 75 nm, about 1 nm to about 100 nm, about 1 nm to about 125 nm, about 1 nm to about 150 nm, about 1 nm to about 175 nm, about 1 nm to about 200 nm, about 1 nm to about 225 nm, about 1 nm to about 250 nm, about 1 nm to about 275 nm, about 0.1 nm to about 1 nm, about 0.1 nm to about 5 nm, about 0.1 nm to about 10 nm, about 0.1 nm to about 15 nm, about 5 nm to about 300 nm, about 10 nm to about 300 nm, about 15 nm to about 300 nm, about 50 nm to about 300 nm, about 75 nm to about 300 nm, about 100 nm to about 300 nm, about 125 nm to about 300 nm, about 150 nm to about 300 nm, about 175 nm to about 300 nm, about 200 nm to about 300 nm, about 225 nm to about 300 nm, about 250 nm to about 300 nm, or about 275 nm to about 300 nm.

The detection biomolecule may be a fragmented detection biomolecule. The fragmented detection biomolecule may be obtained by cleaving or reducing a detection biomolecule using a cleaving agent or may be artificially synthesized. The cleaving agent may be a chemical such as tris(2-carboxyethyl)phosphine, dithiothreitol or 2-mercaptoethanol or may be an enzyme such as a protease. The protease may be an endopeptidase such as but not limited to trypsin, chymotrypsin, elastase, thermolysin, pepsin, glutamyl endopeptidase, ficain, papain, bromelase, calpain, caspase, cathepsin B, chymopapain, etc. It is to be appreciated that the above are only examples of some cleaving agents and are not meant to be limited to just the above.

Where the fragmented detection biomolecule is an antibody fragment, the antibody fragment may be selected from the group consisting of F(ab')$_2$, Fab, Fab', Fd, Fv dAb, camelid, nanobody, isolated complementarity determining region, sFv, scFv and r IgG fragment.

The bioassay may be robust such that the bio-functionalized nanostructure on the substrate may be kept at an ambient temperature for a few days (such as 1 to 3 days) without affecting the fluorescence signal emitted by the inorganic fluorescent particle.

The sample that is suspected of containing the target analyte may be obtained from a patient or may be an environmental sample. Where the sample is obtained from a patient, the body sample may be a sample of ascites fluid, whole blood, serum, bile, saliva or sputum. Where the sample is an environmental sample, the sample may be obtained from water (such as wastewater, reservoirs, lakes, streams, seas or oceans), soil or a plant material in an aqueous solution.

The method may comprise the step of rinsing the nanostructures after each step of immobilizing the capture biomolecule, adding the blocking agent, adding the sample suspected of containing the target analyte, binding the detection biomolecule to the target analyte or conjugating the inorganic fluorescent particle to the detection biomolecule. The rinsing step may be repeated as desired in order to ensure that the reagents and (any unbound or unreacted) agents used in the preceding step are not present in the next step so as to reduce any false-positives or contamination.

The inorganic fluorescent particle may be a semiconductor nanocrystal. The semiconductor nanocrystal may be a quantum dot. The quantum dot may be substantially spherical in shape. The diameter of the substantially spherical particle (or equivalent diameter for a non-spherical particle) may be in the range selected from the group consisting of about 1 nm to about 100 nm, about 1 nm to about 10 nm, about 1 nm to about 20 nm, about 1 nm to about 30 nm, about 1 nm to about 40 nm, about 1 nm to about 50 nm, about 1 nm to about 60 nm, about 1 nm to about 70 nm, about 1 nm to about 80 nm, about 1 nm to about 90 nm, about 10 nm to about 100 nm, about 20 nm to about 100 nm, about 30 nm to about 100 nm, about 40 nm to about 100 nm, about 50 nm to about 100 nm, about 60 nm to about 100 nm, about 70 nm to about 100 nm, about 80 nm to about 100 nm, or about 90 nm to about 100 nm.

The quantum dot may be made from at least one element selected from Group 12, Group 16, Group 2, Group 13, Group 15 or Group 14 of the Periodic Table of Elements. The quantum dot may be made of a material such as, but not limited to, CdO, CdS, CdSe, CdTe, CdSeTe, CdHgTe, ZnS, ZnSe, ZnTe, ZnO, MgTe, MgS, MgSe, MgO, GaAs, GaP, GaSb, GaN, HgO, HgS, HgSe, HgTe, CaS, CaSe, CaTe, CaO, SrS, SrSe, SrTe, SrO, BaS, BaSe, BaTe, BaO, InAs, InP, InSb, InN, AlAs, AlN, AlP, AlSb, AlS, PbO, PbS, PbSe, PdTe, Ge, Si, ZnO, ZnS, ZnSe, ZnTe and combinations thereof.

The quantum dot may be of a core-shell structure. Exemplary shell material include, but are not limited to, ZnO, ZnS, ZnSe, ZnTe, CdO, CdS, CdSe, CdTe, MgS, MgSe, GaAs, GaN, GaP, GaAs, GaSb, HgO, HgS, HgSe, HgTe, InAs, InN, InP, InSb, AlAs, AlN, AlP, AlSb, or combinations thereof, optionally with the inner shell comprising at least one element selected from Group 12, Group 16, Group 2, Group 13, Group 15 or Group 14 of the Periodic Table of Elements. In one embodiment, the quantum dot has an inner core of CdSe and an outer shell of ZnS.

The outer surface of the quantum dot may be further coated with a polymer that may allow conjugation to biomolecules while retaining the optical properties of the quantum dot.

The quantum dot may have an emission wavelength that is substantially different from its excitation wavelength. The quantum dot may have a broad band excitation. The wavelength gap (between the emission wavelength and the excitation wavelength) may be at least 5 nm, at least 10 nm, at least 50 nm, at least 100 nm, at least 150 nm, at least 200 nm, at least 250 nm, at least 300 nm, at least 350 nm, at least 400 nm, at least 450 nm, or at least 500 nm. By having a large wavelength gap, this will ease the separation of the relatively weak photoluminescence from the strong excitation and increase the signal-to-noise ratio.

The fluorescence emitted by the inorganic fluorescent particle may be detected using a fluorescence microscope, an optical detector or a camera. The microscope may be equipped with a charge-coupled device camera and/or a spectrograph.

The nanostructure may be formed on a solid phase substrate. The substrate may be glass, silicon, or a polymer (such as polystyrene) that is strong enough to support the nanostructure which will be present as a plurality of nanostructures on the substrate. Hence, a point-of-care system can be created based on the nanostructures on the substrate, the capture biomolecules, the detection biomolecules and the inorganic fluorescent particle.

The nanostructures may be formed on the substrate by photolithography, deep reactive ion etching, holographic lithography, e-beam lithography, ion-beam lithography, focused ion beam, interferometric lithography, colloidal lithography, nanoimprinting and combinations thereof.

A mold may be used to form the nanostructure onto the substrate.

The nanostructure may be formed from a metal or the nanostructure may be coated with a layer of metal, the metal being one that is capable of resonating with light at a particular wavelength to produce a surface plasmon resonance.

The metal may be selected from the group consisting of Group 13, Group 9, Group 11, Group 6, Group 10, Group 14, Group 4 and Group 12 of the Periodic Table of Elements, as well as their alloys and combinations thereof. The metal may be selected from the group consisting of aluminum, cobalt, copper, gold, indium, molybdenum, nickel, palladium, platinum, silver, tin, titanium, tungsten, zinc, alloys and combinations thereof. In one embodiment, the metal is gold. The height of the metallic nanostructure or metal layer on the nanostructure may be in the range of about 1 nm to about 500 nm, about 1 nm to about 10 nm, about 1 nm to about 50 nm, about 1 nm to about 100 nm, about 1 nm to about 150 nm, about 1 nm to about 200 nm, about 1 nm to about 250 nm, about 1 nm to about 300 nm, about 1 nm to about 350 nm, about 1 nm to about 400 nm, about 1 nm to about 450 nm, about 10 nm to about 500 nm, about 50 nm to about 500 nm, about 100 nm to about 500 nm, about 150 nm to about 500 nm, about 200 nm to about 500 nm, about 250 nm to about 500 nm, about 300 nm to about 500 nm, about 350 nm to about 500 nm, about 400 nm to about 500 nm or about 450 nm to about 500 nm.

Where a metal layer is coated onto the nanostructure, the metal layer may be adhered to the nanostructure via an adhesive layer. The adhesive layer may comprise a metal such as chromium or titanium. The adhesive layer may have a height of about 1 nm to about 50 nm, about 1 nm to about 10 nm, about 1 nm to about 20 nm, about 1 nm to about 30 nm, about 1 nm to about 40 nm, about 10 nm to about 50 nm, about 20 nm to about 50 nm, about 30 nm to about 50 nm, or about 40 nm to about 50 nm.

The exposed surfaces of the nanostructure may be roughened. By exposed surface, this may refer to the top, side or bottom of the nanostructure (as the case may be). The rough surface may aid in the creation of surface plasmons on the nanostructrue. This may be due to the diffraction of light into higher orders as it contacts the rough surface.

The nanostructure may be in the form of, for example, nanoholes, nanopillars, or gratings. The nanoholes may extend towards and within the interior of the substrate. The depth of the nanoholes, as measured from the opening of the nanohole to the bottom of the nanohole may exemplarily be in the range of about 1 nm to about 500 nm, about 1 nm to about 10 nm, about 1 nm to about 50 nm, about 1 nm to about 100 nm, about 1 nm to about 150 nm, about 1 nm to about 200 nm, about 1 nm to about 250 nm, about 1 nm to about 300 nm, about 1 nm to about 350 nm, about 1 nm to about 400 nm, about 1 nm to about 450 nm, about 10 nm to about 500 nm, about 50 nm to about 500 nm, about 100 nm to about 500 nm, about 150 nm to about 500 nm, about 200 nm to about 500 nm, about 250 nm to about 500 nm, about 300 nm to about 500 nm, about 350 nm to about 500 nm, about 400 nm to about 500 nm or about 450 nm to about 500 nm. The size of the nanoholes may be in the range of about 1 nm to about 1000 nm, about 1 nm to about 100 nm, about 1 nm to about 200 nm, about 1 nm to about 300 nm, about 1 nm to about 400 nm, about 1 nm to about 500 nm, about 1 nm to about 600 nm, about 1 nm to about 700 nm, about 1 nm to about 800 nm, about 1 nm to about 900 nm, about 100 nm to about 1000 nm, about 200 nm to about 1000 nm, about 300 nm to about 1000 nm, about 400 nm to about 1000 nm, about 500 nm to about 1000 nm, about 600 nm to about 1000 nm, about 700 nm to about 1000 nm, about 800 nm to about 1000 nm, or about 900 nm to about 1000 nm.

The nanopillars may extend from the surface of the substrate such that the height of the nanopillars, as measured from the base to the top of the nanopillar may exemplarily be in the range of about 1 nm to about 500 nm, about 1 nm to about 10 nm, about 1 nm to about 50 nm, about 1 nm to about 100 nm, about 1 nm to about 150 nm, about 1 nm to about 200 nm, about 1 nm to about 250 nm, about 1 nm to about 300 nm, about 1 nm to about 350 nm, about 1 nm to about 400 nm, about 1 nm to about 450 nm, about 10 nm to about 500 nm, about 50 nm to about 500 nm, about 100 nm to about 500 nm, about 150 nm to about 500 nm, about 200 nm to about 500 nm, about 250 nm to about 500 nm, about 300 nm to about 500 nm, about 350 nm to about 500 nm, about 400 nm to about 500 nm or about 450 nm to about 500 nm. The size of the nanopillars may be in the range of about 1 nm to about 1000 nm, about 1 nm to about 100 nm, about 1 nm to about 200 nm, about 1 nm to about 300 nm, about 1 nm to about 400 nm, about 1 nm to about 500 nm, about 1 nm to about 600 nm, about 1 nm to about 700 nm, about 1 nm to about 800 nm, about 1 nm to about 900 nm, about 100 nm to about 1000 nm, about 200 nm to about 1000 nm, about 300 nm to about 1000 nm, about 400 nm to about 1000 nm, about 500 nm to about 1000 nm, about 600 nm to about 1000 nm, about 700 nm to about 1000 nm, about 800 nm to about 1000 nm, or about 900 nm to about 1000 nm.

The gratings may be a series of parallel disposed grooves or slit formations provided on the surface of the substrate. The gratings may be in the shape of a semi-circle, square or rectangle when viewed in the cross-section. The spacing between each pair of gratings may exemplarily be in the range of a few nanometers to about 10 micrometers. The height of the gratings may exemplarily be in the range of about 1 nm to about 5,000 nm while the width may exemplarily be in the range of about 1 nm to about 5,000 nm. Further, it is to be appreciated that the type of nanostructure is not limited to the above and may include any roughened metal surface (such as due to random deposition of gold or silver islands, or chemically deposited metal nanoparticles on the chip), or other kinds of indented metal films, as long as plasmonics can be generated.

As each geometrical nanostructure has different surface coverage (for immobilizing the capture biomolecule) and volume coverage, each geometry of the nanostructure may result in different plasmonic field coverage (in terms of depth, breadth and/or volume). Hence, nanostructures that have a greater surface and/or volume coverage will have higher plasmonic field coverage, leading to greater excitation of the plasmonics which in turn results in better and more sensitive detection of the target analyte. It has been found that nanopillars may have higher surface and/or volume coverage as compared to nanoholes, leading to better sensitivity when nanopillars are used.

The plurality of nanostructures may be present as an array on the substrate. The nanostructures may be placed at a specific distance from each other, forming an ordered array, or may be placed at random distance from each other, forming a disordered (or random) array. Where the nanostructures are placed at a specific distance from each other, the pitch (the length of the center-to-center spacing between the nanostructures) may be in the nanoscale range or in the microscale range A light source may be used to excite the surface plasmons for generating the surface plasmon resonance effect. The light beam may be transmitted from a halogen lamp, a light emitting diode, a fluorescent lamp or a diode laser. The light beam may be in the visible light region, the infra-red region or ultra-violet region of the Electromagnetic Spectrum. The light beam may be a laser beam. The laser beam may be emitted from a laser light source. The laser beam may be substantially s-polarized, substantially p-polarized or substantially unpolarized. The wavelength of the light beam may be in the range of about 500 nm to about 1200 nm.

The type of surface plasmon resonance may be surface plasmon resonance, localized surface plasmon resonance or co-excitation of surface plasmon resonance and localized surface plasmon resonance.

The light source may be used to excite the surface plasmons at an integration time in the range of about 0.1 ms to about a few hours. The integration time may be about 20 ms, about 50 ms, or about 100 ms. By exposing the bioassay for a longer period of time to the light source, higher optical signal of the inorganic fluorescent particle may be detected. Nevertheless, even at a low integration time, the fluorescence emitted by the inorganic fluorescent particle may be detected if the concentration of the target analyte is high enough. As an example, a target analyte having a concentration as low as 1 ng/ml can be detectable at 20 ms exposure time.

There is also provided a kit for detecting the presence or absence of a target analyte in a sample comprising:
  a substrate having a nanostructure thereon for immobilizing a capture biomolecule on or within the nanostructure, the capture biomolecule being capable of binding specifically to the target analyte, if present in the sample;
  a detection biomolecule capable of binding specifically to the target analyte, if present in the sample; and
  an inorganic fluorescent particle capable of conjugating with the detection biomolecule to form a detection reagent,
  wherein upon excitation by a light source, the nanostructure is capable of generating a surface plasmon resonance effect to thereby enhance the fluorescence emitted by the detection reagent when bound to the target analyte, if present in the sample.

The bioassay may be robust and may have a long shelf-life, the bioassay may be regenerated using an appropriate solvent. The nanostructures modified by the capture biomolecule may be kept at a low temperature or room temperature for a number of days without substantially affecting the performance of the bioassay.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 1 is a schematic diagram showing the manufacture of a sandwich assay for detecting the absence or presence of a target analyte.

FIGS. 2A-2B show reflection, transmission and absorption spectra and the near-field distribution at a wavelength of 530 nm for (a) gold nanohole array (FIG. 2A) and (b) gold nanopillar array (FIG. 2B), both of which are provided on a glass substrate and illuminating light provided from the biosample side.

FIGS. 3A-3E show the scanning electron microscope (SEM) images of (a) gold nanohole array (FIG. 3A) and (b) gold nanopillar array (FIG. 3B) at a scale of 10,000× as well as comparisons of the measured and designed transmission spectra of (c) gold nanohole array (FIG. 3C) (the simulation is for gold nanohole array at 140 nm diameter) and (d) gold nanopillar array (FIG. 3D) (the simulation is for gold nanopillar array at 140 nm square length) while FIG. 3E shows the comparison of the simulated power absorption spectra of the square and round gold nanopillars.

FIGS. 5A-5D show a number of atomic force microscope (AFM) images of the gold nanohole array. FIG. 5A shows fabricated nanoholes without any biomaterial, where the white spots are some photoresist residue that existed before the UV/O3 cleaning conducted prior to the biofunctionalization, FIG. 5B shows gold nanoholes with cleft antibody, in which the cleft antibody formed a homogenous layer on the gold while FIGS. 5C and 5D show gold nanoholes with the quantum dots sandwich bioassay, taken at different angles of view.

FIG. 6A shows fabricated nanopillars without any biomaterial, FIG. 6B shows gold nanopillars with cleft antibody while FIGS. 6C and 6D show gold nanopillars with the quantum dots sandwich bioassay, taken at different angles of view.

DETAILED DESCRIPTION OF DRAWINGS

Figure 3A:
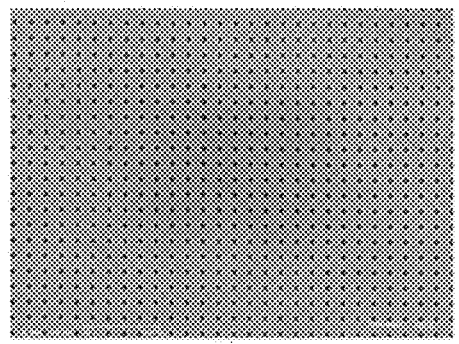
Figure 3B:
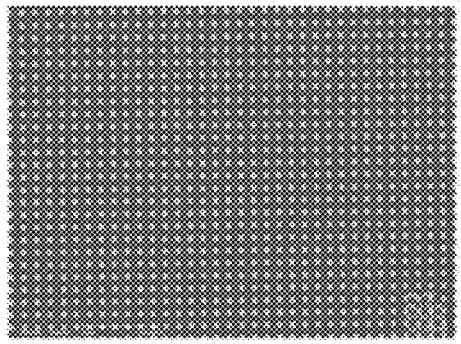
Figure 3C:
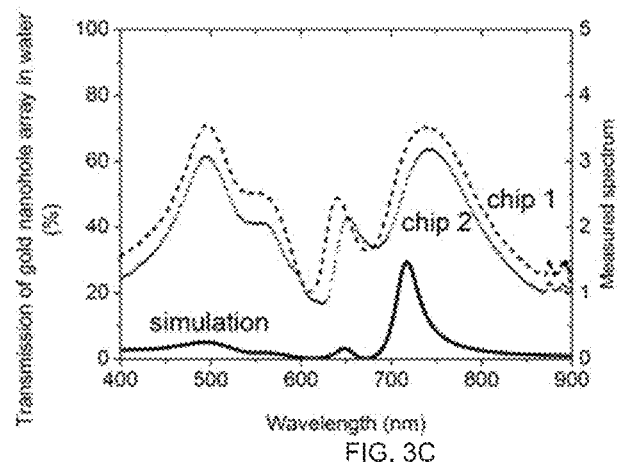
Figure 3D:
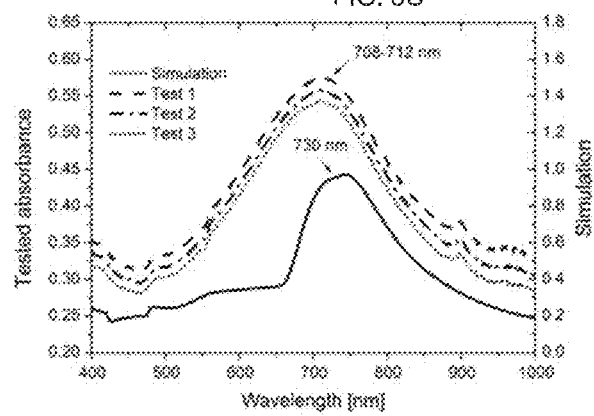
Figure 3E:
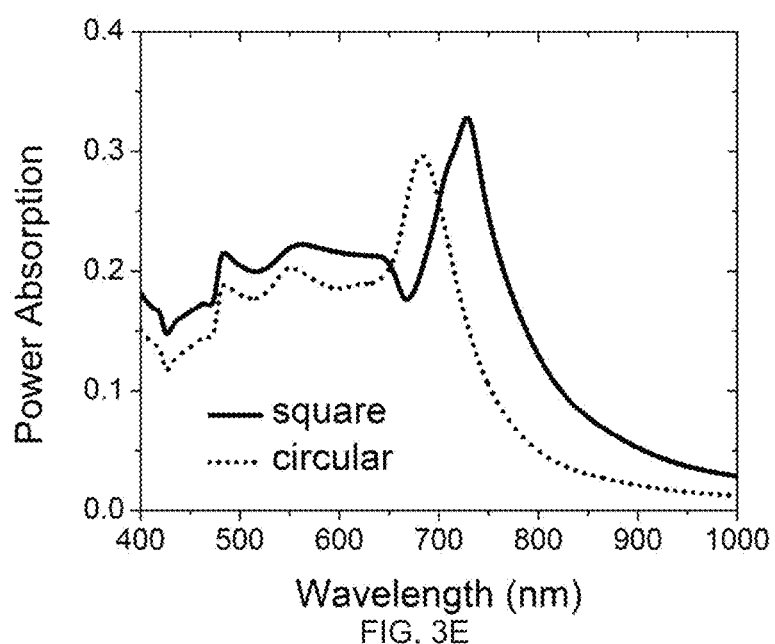

Referring to FIG. 1, there is provided a process 100 showing the manufacture of a sandwich assay for detecting a target analyte. Here, a plurality of nanostructures 2 are provided on a solid-phase substrate 4 for immobilizing capture biomolecules 10 which had been cleaved or fragmented out from their corresponding whole biomolecules 6 using a cleaving agent 8. Unbounded areas of the nanostructures 2 are then subjected to a blocking agent 12 to block free immobilization sites on the nanostructures 2 or substrate 4 that are not covered by the capture biomolecules 10 so as to avoid non-specific binding of a target analyte 14 on the surface (of the nanostructures 2 or substrate 4). Following which, the target analyte 14 is added and allowed to bind with the capture biomolecule 10 that is immobilized on the nanostructure 2. A detection biomolecule 16 having a moiety that is capable of conjugating with an inorganic fluorescent particle 18 is subsequently added. The moiety present on the detection biomolecule 16 then binds to a partner moiety on the inorganic fluorescent particle 18. The resultant capture antibody 10/target analyte 14/detection biomolecule 16/inorganic fluorescent particle 18 then forms a sandwich assay on the solid-phase substrate 4. Upon excitation of the surface plasmons on the nanostructure 2 to create localized surface plasmon resonance (LSPR) on the surfaces of the nanostructure 2, the LSPR enhances the fluorescence emitted by the inorganic fluorescent particles such that the enhanced fluorescence can be easily detected by a fluorescent detector to determine the absence or presence of the target analyte 14.

In one embodiment, the plurality of nanostructures 2 are gold nanostructures which are provided on a solid-phase substrate 4 such as a glass substrate. The capture biomolecules 10 are fragments of a capture antibody that is specific to a target analyte 14 such as prostate specific antigens (PSA). The blocking agent 12 is bovine serum albumin. The detection biomolecule 16 having a moiety is biotinylated detection antibody that is able to bind to a different binding site on PSA while the inorganic fluorescent particle is a streptavidin conjugated quantum dot. Due to the binding between the biotin (of the biotinylated detection antibody) and streptavidin (of the streptavidin conjugated quantum dot), a sandwich assay made up of fragmented PSA capture antibody/PSA/PSA detection antibody/quantum dot is formed. The fluorescence emitted by the bound quantum dot (which is enhanced by the localized surface plasmon resonance on the gold nanostructure upon excitation of a light source) is then detected using a fluorescence detector to determine the absence or presence of the PSA.

EXAMPLES

Non-limiting examples of the invention will be further described in greater detail by reference to specific Examples, which should not be construed as in any way limiting the scope of the invention.

Example 1

Nanostructure Design, Fabrication and Characterization

Nanostructure Design: Here, two types of exemplary gold nanostructure arrays were designed and simulated through the COMSOL software, which is based on the finite element method to provide total plasmonic field information, including the reflection, transmission and absorption light intensity as well as the plasmonic near-field distribution around the gold nanostructures at each wavelength. The objective of the plasmonic nanostructure design is to maximize the quantum dot (QD) photoluminescence by the electromagnetic enhancement of the plasmonic resonances. For the gold nanostructure array, only a unit cell composed of one gold nanostructure embedded in a square whose length equals to the array pitch needs to be calculated. In the cases of round or square gold nanostructures, only a quarter of the unit cell was simulated due to the geometrical symmetry.

In the simulation, the frequency-dependent dielectric function of gold was taken from Palik handbook, and the refractive indices for glass, air and water were taken as 1.52, 1.0, and 1.33, respectively.

To ensure the accuracy of the simulations, the sum of the calculated reflected, transmitted and absorbed power was checked against the input incident power, and they were the same within <2% error.

Fabrication: Following the above nanostructure design, the gold nanostructure arrays were then fabricated.

Gold Nanohole array: The gold nanohole array was fabricated by mass fabrication via nanoimprinting on 4" wafer. The designed gold nanopatterns were first written by e-beam lithography on a 4" silicon wafer. After photoresist development, a seed metal layer was coated on the gold surface, and a nickel layer up to 300 µm thick was electroplated on the silicon wafer. After separation, a 4" nickel mold was obtained. The nickel mold was UV nanoimprinted on a 4" glass wafer coated with UV curable photoresist. After nanoimprinting, a gold film was deposited on the nanoimprinted photoresist, and the gold nanostructures were obtained after photoresist lift-off. Finally, the glass wafer was diced into localized surface plasmon resonance (LSPR) chips. For the gold nanohole chips, each chip was 1 cm×1 cm with the central 1.8 mm×1.8 mm area covered by gold nanoholes and the remaining areas covered with gold film. In the following experiments, the gold film was used as a reference to show the importance of having the LSPR enhancement in the QD bioassay for analyte detections.

The resultant gold nanohole array has a pitch of 400 nm, size of 140 nm×140 nm and depth of 55 nm (the metal layer includes 5 nm of chromium as the adhesive layer and 50 nm of gold for plasmonic generation).

Gold Nanopillars Array: The gold nanopillars were fabricated by direct e-beam writing on a 4" glass wafer, followed by photoresist development, gold film coating, and photoresist lift-off, and the glass wafer was later diced into chips. Each gold nanopillar array chip was 1 cm×1 cm with the central 0.9 mm×0.9 mm area covered by gold nanopillars and the remaining areas covered with gold film. In the following experiments, the gold film was used as a reference to show the importance of having the LSPR enhancement in the QD bioassay for analyte detections.

The resultant gold nanopillar array has a pitch of 320 nm, size of 140 nm×140 nm and height of 55 nm (the metal layer includes 5 nm of chromium as the adhesive layer and 50 nm of gold for plasmonic generation).

Characterization: The nanoholes and nanopillars arrays were then characterized. FIG. 2 presents the reflection, transmission, absorption spectrum, and near-field distributions of (a) gold nanohole array and (b) gold nanopillar array when the incident light is from the buffer side, same as the experimental condition. The near-field distributions at 530 nm (which is excitation wavelength of the quantum dots) show that both types of nanostructures have a strong field enhancement of up to 10 times at the edges of the top and bottom surfaces. Due to these enhanced fields, the quantum dots could be more efficiently excited, which greatly improves on the sensitivity of the bioassay. Promising sensitivity improvement is observed for the two demonstrated nanostructures in the bioassay experiments. To optimize the bioassays further, it is envisaged that under an ideal condition in which the plasmonic peak wavelength matches the excitation wavelength of the quantum dots, the plasmonic field enhancement will be maximized and higher sensitivity or lower detection limit can be achieved.

FIG. 3 shows the SEM images of the (a) gold nanohole array and (b) gold nanopillar array. The transmission spectra of these LSPR nanostructure chips were measured by optical spectrometer, and they were highly matched to their corresponded simulation results, proving the high quality of the fabricated LSPR nanostructure chips. However, in FIG. 3(c), the simulation spectrum is for round gold nanohole array, where the simulation has the plasmonic peak slightly blue shifted. On the country, in FIG. 3(d), the simulation spectrum is for square nanopillars, where the simulation has the plasmonic peak red shifted. This can be explained by the comparison of the power absorption spectra of the gold nanopillars in FIG. 3(e), where the gold nanopillars are with the same pitch of 320 nm and the same height of 50 nm, but the square one is with a length of 140 nm, and the round one is with a diameter of 140 nm. FIG. 3(e) indicates that the plasmonic peak wavelength might blue shift up to 50 nm when the shape is turned from square to circular. Since the fabricated gold nanoholes and nanopillars are in square shape with some round corners, the measurement spectra should red shift compared with the simulated round ones and blue shift compared with the simulated square ones.

FIG. 4 shows simulations of the transmission and plasmonic absorption spectra for (a) nanoholes and (c) nanopillars as well as plasmonic field distributions for (b) nanoholes and (d) nanopillars. The simulations of the transmission and plasmonic absorption (near-field) spectra in FIGS. 4(a) and (c) showed that there is a blue shift for the round nanostructures compared to the square ones for both nanoholes and nanopillars. The adhesive chromium layer was not considered in the simulations, because this layer only slightly reduces the plasmonic intensity without shifting the peak wavelengths much. Both the square and round shapes of gold nanohole and gold nanopillar arrays were simulated. As shown in the SEM images in FIG. 3(a) and FIG. 3(b), the fabricated gold nanostructures mostly maintain the original square shape in e-beam writing, and only a small part in the corner become round. Therefore, the measured transmission peaks/dips are in between the simulated ones for square and round nanostructures. Simulations in FIG. 4(b) and FIG. 4(d) showed that both the gold nanohole and nanopillar arrays will generate plasmonic amplification at the wavelength of 540 nm for QD excitation, and they have similar field distributions at the top and bottom rims of the nanostructures. At the wavelength of 540 nm, the gold nanoarrays have 4-8 (at the top rims) and 11-20 times (at the bottom rims) of enhancement, and the gold nanopillar array has 20-25% higher enhancement over the gold nanohole array. Considering the difficulty for analytes to reach the bottom of the nanostructures, the plasmonic enhancement on the top rims contributes more to the QD emissions. FIG. 4(d) also exemplifies that at the wavelength of 540 nm, the round and square shaped nanostructures have similar plasmonic intensity at the bottom rims, but the square ones have a 50% stronger electromagnetic field at the top rims. As presented in FIGS. 4(a), (c) and (d), the strongest plasmonic peak for the gold nanohole array is at 650 or 750 nm while that for the nanopillar array is at the wavelength of 740 nm.

Figure 4A:
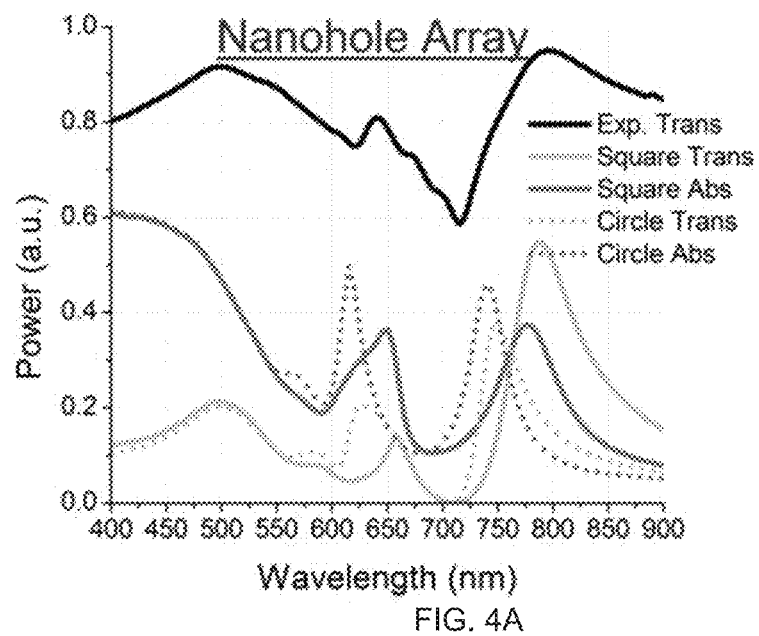
FIGS. 4A-4D show simulations of the transmission and plasmonic absorption spectra for (a) nanoholes (FIG. 4A) and (c) nanopillars (FIG. 4C) as well as plasmonic field distributions for (b) nanoholes (FIG. 4B) and (d) nanopillars (FIG. 4D).
Figure 4B:
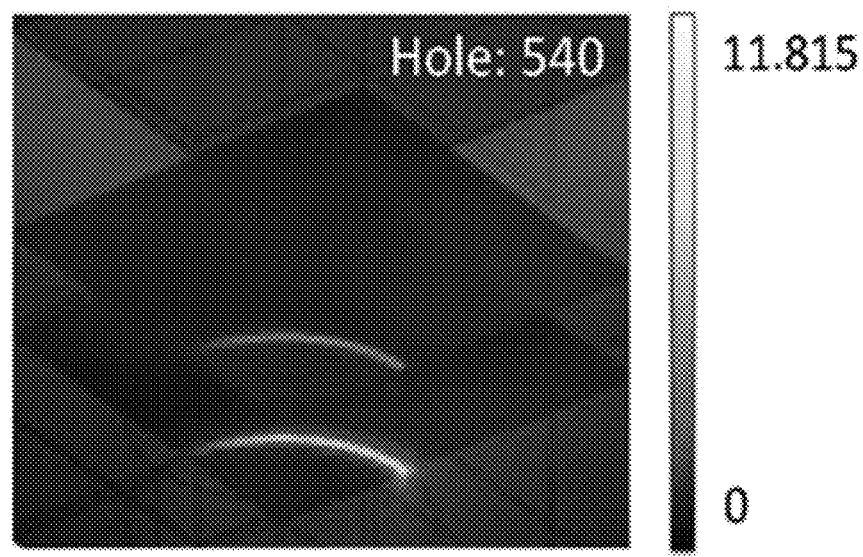
Figure 4C:
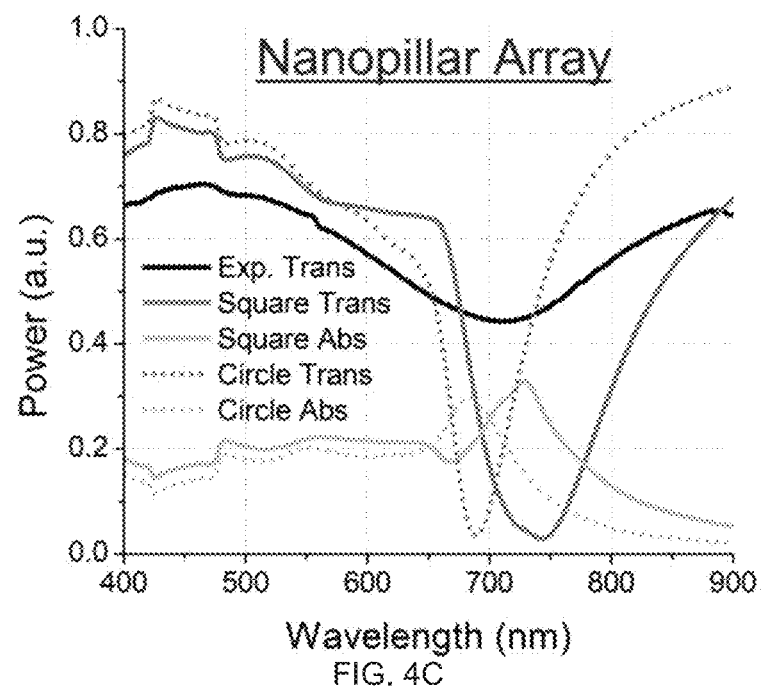
Figure 4D:
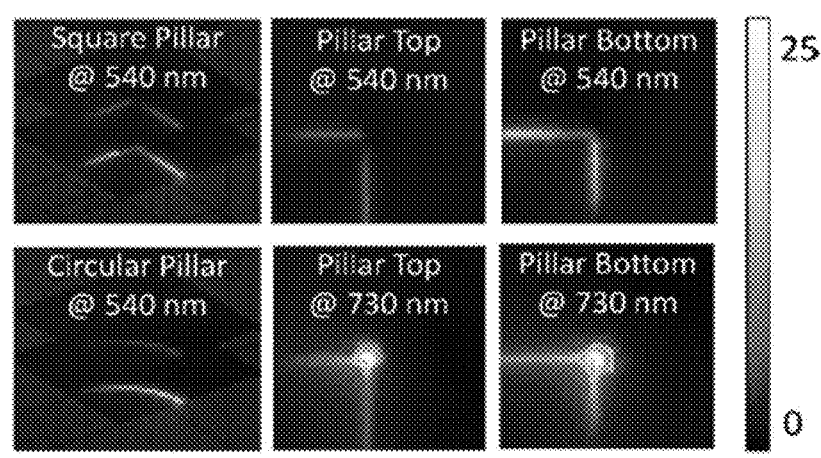
Figure 6A:
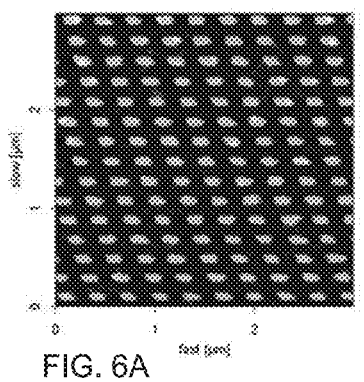
FIGS. 6A-6D show a number of AFM images of the gold nanopillar array.
Figure 6B:
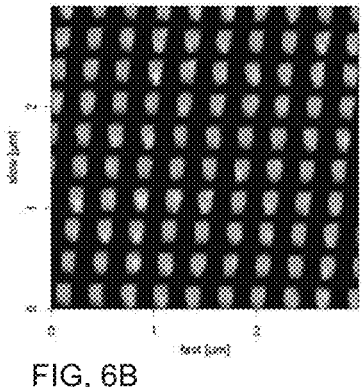
Figure 6C:
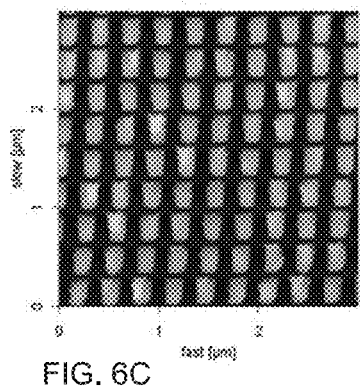
Figure 6D:
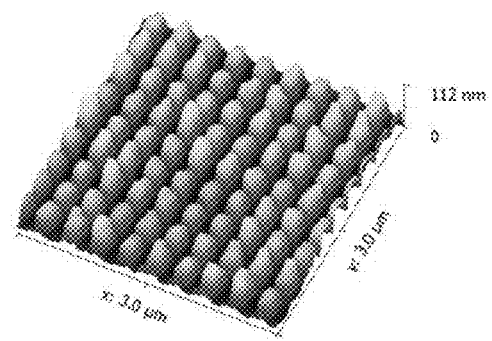

FIG. 4(b) and FIG. 4(d) demonstrate that the plasmonic field decreases sharply as the distance to the gold nanostructure reduces. However, the fluorescence enhancement is the product of excitation enhancement and the dye's quantum yield defined as the fraction of radiative transitions from excited to ground state to the total decay rate. The quantum yield decreases up to zero as the dyes approach to the gold nanostructure surface, which is totally quenched by plasmon. For gold nanostructures, the optimal distance for maximal fluorescence enhancement is about 10-15 nm, which was well controlled herein by the sandwich immunoassay fabrication.

Example 2

Biofunctionalization of Nanostructures

Materials: Purified human prostate specific antigen (PSA), PSA monoclonal capture antibody G3D6 (cAb) and PSA monoclonal detection antibody G1E3 (dAb) were purchased from BBI Solutions (of Sittingbourne, UK). Qdot® 655 streptavidin conjugate (QD-655) and NHS-PEG4-biotin were purchased from Life Technologies (of Singapore). BSA was purchased from Sigma-Aldrich (of Singapore).

HEPES buffer (10 mM HEPES, 150 mM NaCl, prepared) was used as dilution buffer for PSA antibody immobilization; HBS buffer (HEPES, with 3.4 mM EDTA, 0.05% P20) was used as binding buffer for PSA detection.

Reduction of Capture Anti-PSA (cAb) with TCEP: TCEP solution was prepared at 50 mM (2.5 mg dissolved in 174 μL of water), and diluted to 250 μM. 5 μL of the diluted TCEP solution was added to 50 μL of the PSA antibody in PBS (1.26 mg/ml, 8.4 μM) and incubated at room temperature for 30 minutes. After reaction, the mixture was purified by G25 column. The purified cleft anti-PSA (cAb-SH) was stored at 4° C. and diluted with HEPES buffer before use.

The Biotinylation of Detection Anti-PSA: The detection PSA antibody (dAb) was buffer changed against PBS (pH 7.2) to 2 mg/ml. 1 μL of NHS-PEG4-biotin (5 mM) was added to 50 μL of the dAb solution and kept at room temperature for 30 minutes. The biotinylated dAb (biotin-dAb) was purified by G25 column and stored at 4° C. until use.

Immobilize TCEP Reduced Anti-PSA: A gold nanostructure chip was treated in a UV/O$_3$ chamber for 7 min. The freshly cleaned chip was rinsed with water and then immersed in the diluted cAb-SH solution (50 μg/ml in HEPES) at 4° C. overnight. After the chip was cleaned by HEPES, BSA solution (3 mg/ml) was applied onto the chip surface for 10 minutes to block the cAb-SH uncovered area. The chip was rinsed 3 times with HEPES buffer to remove the unbound proteins.

Sandwiched PSA Detection Analysis with Quantum Dots 655: PSA was prepared in different concentrations in HBS (100 ng/ml, 50 ng/ml, 10 ng/ml, 5 ng/ml, 1 ng/ml, 100 pg/ml). A drop (50 μl) of PSA solution was put on the fabricated area of the chip, which was pre-modified with cAb-SH, for 1 hour at room temperature (about 25° C.). The chip was then rinsed with HBS 3 times, followed by adding a drop (20 μl) of biotin-dAb (20 μg/ml) for 30 minutes. After that, the chip was rinsed again with HBS, followed by adding a drop (20 μl) of QD-655 (20 nM) for 30 min. After washing away the QD-655, the sandwiched cAb-SH/PSA/biotin-dAb/QD-655 sensor chip was checked under a fluorescent microscope. As a control, PSA was not added onto the cAb-SH modified sensor chip, but biotin-dAb and QD-655 were added in the same sequence. The cAb sensor surface can be regenerated by applying 10 mM glycine (pH 2.5) for 1 minute to remove PSA/biotin-dAb/QD-655.

cAb-SH Conformation Measured by DPI: To investigate the conformation of the cleft anti-PSA, dual polarization interferometry (DPI) was used to measure its thickness, density, refractive index, and mass value. DPI is an interferometer based technology using two polarized light (transverse-magnetic (TM) and transverse-electric (TE)) to detect on the sensor chip simultaneously, thus besides providing the real-time detection of the chemical binding kinetics, the conformation information of each layer of the chemicals can also be derived from the measurement.

To immobilize the cAb-SH for DPI detection, an amine modified DPI sensor chip was treated with Sulfo-GMBS to convert the surface functionality to maleimide, then cAb-SH was immobilized on the surface by thiol-maleimide covalent linkage. The surface functionalization was conducted outside the DPI, after that, the chip was cleaned and inserted into the instrument for real-time measurement.

In DPI experiments, time-resolved sensorgram of the cAb-SH immobilization shows that the injection of cAB-SH leads to a fast mass, thickness, RI and density increase, which reflects significant attachment of the cAb-SH onto the sensor surface. When the surface was stabilized, the measured thickness was 7.79 nm and the mass was 2.47 ng/mm$^2$, with a density of 0.32 g/cm$^3$ and reflective index of 1.39. The thickness value provided a direct indication that the cleft antibody adopted a site-specific orientation, which is more than a half of the long axis of the Y shape molecule, based on the reported X-ray crystallography that antibody is a Y-shaped molecule of overall dimension approximately 14.2 nm×8.5 nm×4.0 nm. In addition, as derived from the mass value, each cAb-SH occupied around 100 nm$^2$, which indicated that the cleft antibody almost formed a monolayer on the surface. The mass value of 2.47 ng/mm$^2$ was also more than a half of the reference value of 3.70 ng/mm$^2$ reported for end-on antibody layer.

AFM Characterization of the Biological Surface: A Nanowizard II instrument (JPK Instruments AG, Berlin, Germany) equipped with NanoWizard head and controller was used for the experiments. A triangular shaped silicon nitride cantilevers (Nano World, PNP-TR) were used throughout the scanning and the spring constant was calibrated using the thermal noise method, in the range of 0.07-0.09 N/m. The experiments were performed in HBS buffer, using a fluid cell and letting the system equilibrate for 30-60 minutes.

The quantitative Imaging mode (QITM) in liquid was performed for the imaging. The QITM is a force spectroscopy based imaging mode enabling the user to have the full control over the tip-sample force at each pixel of the image and the lateral forces can be greatly minimized, which makes nondestructive imaging straightforward.

The AFM characterized morphologies of the LSPR nanostructure chip after fabrication, after cleft antibody immobilization, and after the quantum dot conjugation in forming the sandwich bioassay are presented in FIG. 5 and FIG. 6 for the gold nanohole array and nanopillar array, respectively. These images indicate successful biofunctionalization of the QD bioassay, and provide the surface and volume coverage information of the QD bioassay on the gold nanostructures.

Additionally, FIG. 5 shows that the QDs piled up to 320 nm on some areas of the gold nanohole array. This is because when two QDs were close together with less stringent washing, biotin on one QD conjugated to the streptavidin of the other QD and formed closely-packed QD layers. QD-655 with streptavidin is a nano-rod of 13.1±2.8×6.3±0.9 nm, equivalent to a sphere with radius r=4.6 nm. Assuming that the QDs are closely-packed spheres, for the nanoholes with 400 nm critical length of gold surface, the maximum QD height will be 280 and 323 nm, respectively, for the cubic and hexagonal closely packed arrangements. Considering the QDs are actually nanorods and might not be ideally closely-packed, the actual QD thickness of 245-255 nm (320 nm minus the gold/chromium thickness of 55 nm and a rough cAb/PSA/dAb/QD thickness of 10-20 nm) is reasonable.

FIG. 6 displays the AFM images of the sandwich immunoassay on the gold nanopillar array. FIG. 6(c) shows that the QD height on the top of the bioassay is about 45-55 nm (120 nm minus 55 nm of metal and 10-20 nm of the cAb-PSA-dAb-QD complex), far below the possible heights of 98 and 113 nm when the QDs were fully closely-packed in cubic or hexagonal arrangements on top of the nanopillar with a critical length of 140 nm. The AFM image verifies that the QD aggregation is far less for the gold nanopillars compared to the nanoholes, probably due to its ease of flushing and removal of the unbound substances.

Fluorescence Microscopic Detection: To record fluorescent images and measure spectra of the QD emissions, a fluorescent microscopy setup was used. The setup consists of Nikon Ti Eclipse fluorescent microscope equipped by EMCCD camera (iXON EMCCD, Andor) which helps to obtain very low fluorescent signals. The microscope is connected to a spectrograph (Andor Sherlock 300) equipped with CCD detector 1024×512 (Newton 920 CCD detector, Andor). Both camera and detector were cooled down to −70° C. to reduce noise. A mercury lamp of 130 W was used as an excitation light source. Excitation wavelength 530 nm and emission signal >600 nm were obtained by utilizing a beam splitter consisting of band-pass filter 540/25 nm, dichroich beam splitter long-pass 565 nm, and band-pass filter 605 nm. The biggest advantage of the current setup is that registration of image and fluorescent spectra can be obtained from the same area. The objective lenses used for this experiment was plan fluor 20×, 0.45 NA. Exposure time used was 20, 50, or 100 ms, and the input slit was 500 μm.

The QDs were excited at a wavelength of 530 nm, which is intentional to ensure that there is a large gap between the excitation wavelength and the emission wavelength.

Example 3

Bioassay Performance

Figure 7A:
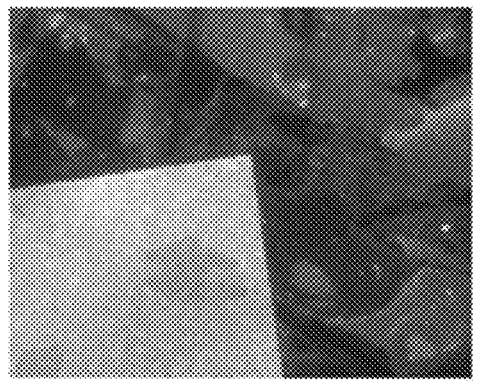
FIGS. 7A-7C show fluorescent images of quantum dots for PSA detection on gold nanohole array with (a) 100 ng/ml (FIG. 7A) and (b) 1 ng/ml (FIG. 7B) of PSA as well as an overlay spectra in FIG. 7C. The integration time was 100 ms.
Figure 7B:
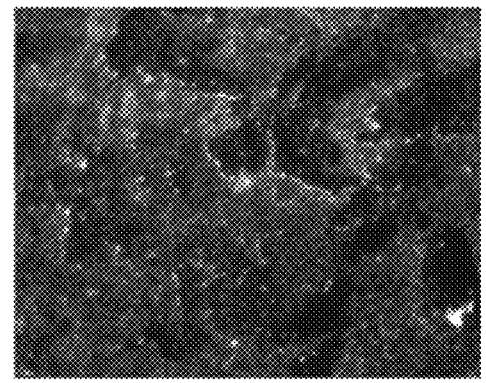
Figure 8A:
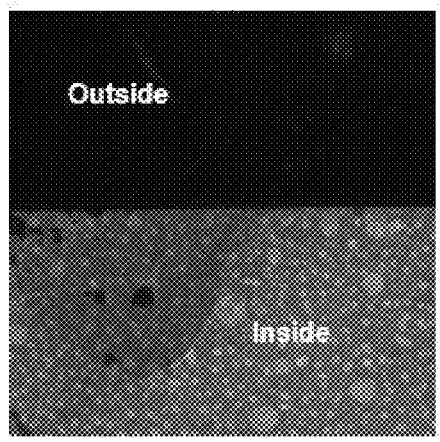
FIGS. 8A-8F show fluorescent images of quantum dots for PSA detection on gold nanohole array at PSA concentrations of (a) and (b) 100 ng/ml (FIGS. 8A and 8B), (c) 10 ng/ml (FIG. 8C), (d) 1 ng/ml (FIG. 8D), (e) 100 pg/ml (FIG. 8E) and (f) 10 pg/ml (FIG. 8F). The integration time was 20 ms.
Figure 8B:
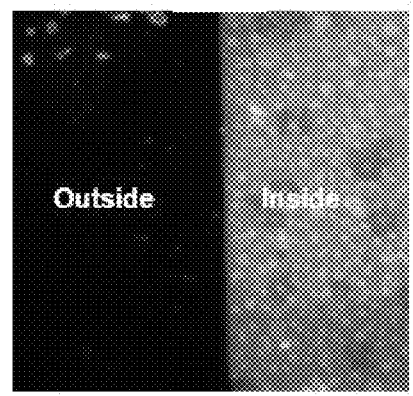
Figure 8C:
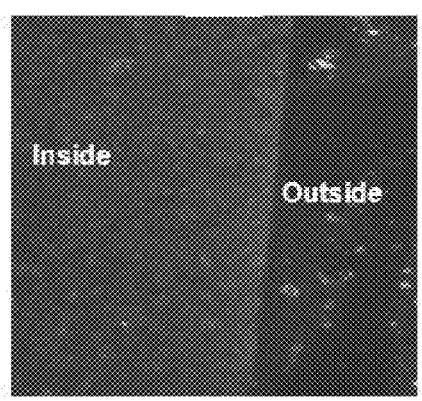
Figure 8D:
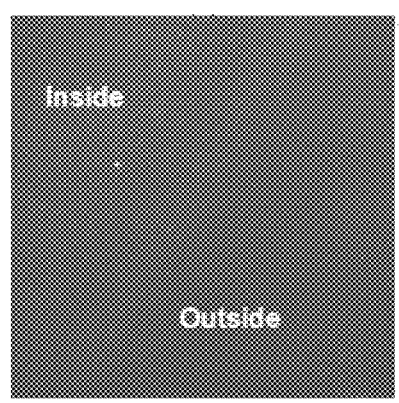
Figure 8E:
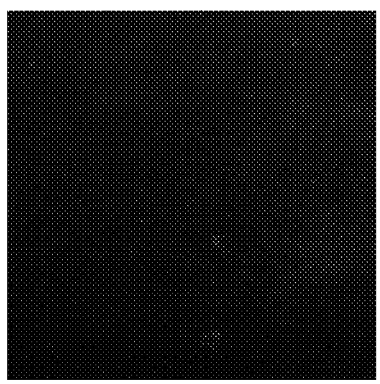
Figure 8F:
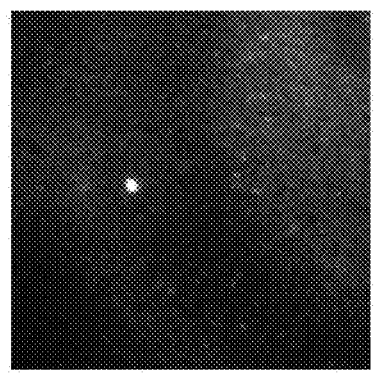

Gold Nanohole Array: As shown in the typical fluorescence images of gold nanohole array with quantum dot bioassay in FIGS. 7(a) and 7(b) (for 100 ms of fluorescence integration time) and FIG. 8 (for 20 ms of the integration time), the inside gold nanohole area showed much stronger fluorescence emission than the outside gold film, due to the plasmonic enhancement provided by the gold nanoholes. The fluorescence difference between outside and inside reduced with the PSA concentration reduction. As shown in FIGS. 8(a) and 8(b), 100 ng/ml of PSA induced fluorescence showed significant difference between gold nanohole area and its outside. When the PSA concentration reached 1 ng/ml (FIG. 8(d)), the fluorescence induced by quantum dots was hard to be discerned. In the control experiment (a gold nanohole array chip but with no PSA added in the sandwich assay), the image was totally dark, which means very low non-specific binding in this quantum dot bioassay.

Figure 9A:
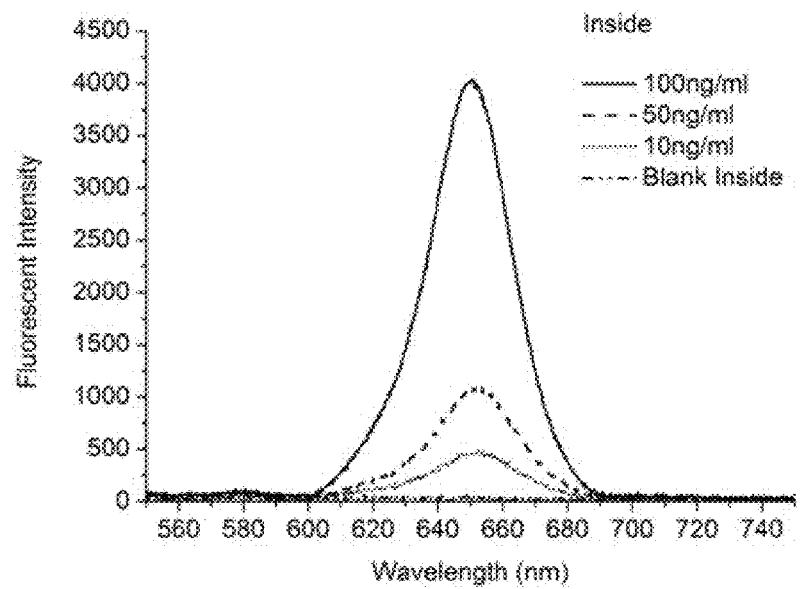
FIGS. 9A-9B show overlay spectra of the LSPR nanohole chips with quantum dots bioassay for different concentrations of PSA for (a) inside (FIG. 9A) and (b) outside of the gold nanohole areas (FIG. 9B). The integration time was 20 ms.
Figure 9B:
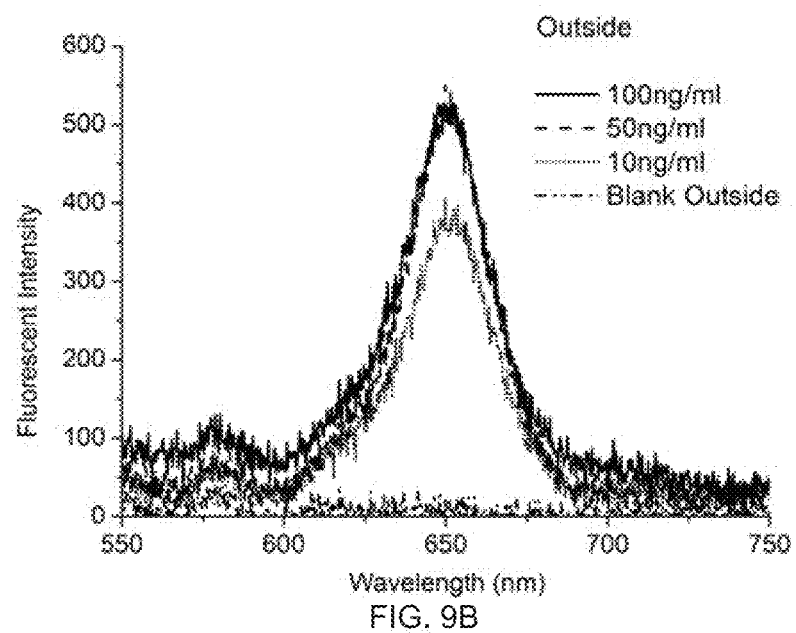

In different experiments, the light signal was integrated with different time span to check the influence of the integration time, and it is found that longer exposure time tended to give higher optical signals, but with 20 ms of the integration time, the quantum dot bioassay already demonstrated good experimental results. Typical fluorescence spectra of the quantum dot bioassays inside and outside the gold nanohole array are plotted in FIG. 7(c) and FIG. 9 for 100 ms and 20 ms of integration time respectively, as analyzed from the fluorescence imaging by the spectrometer.

Figure 7C:
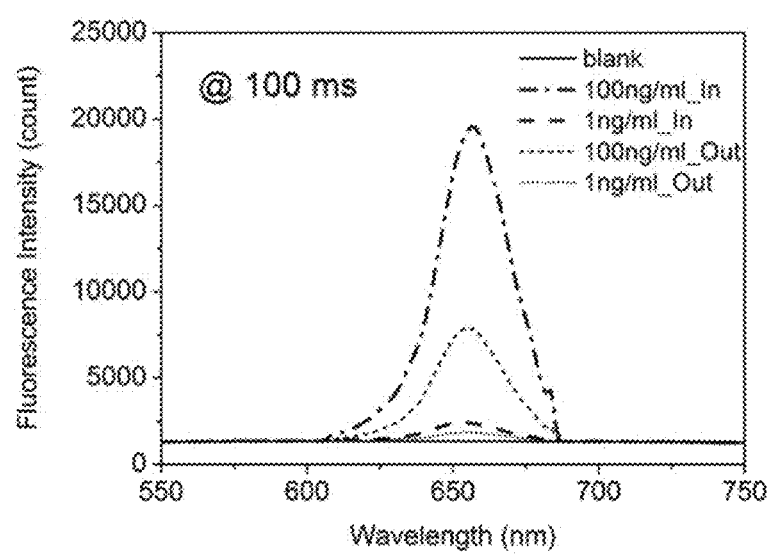
Figure 10:
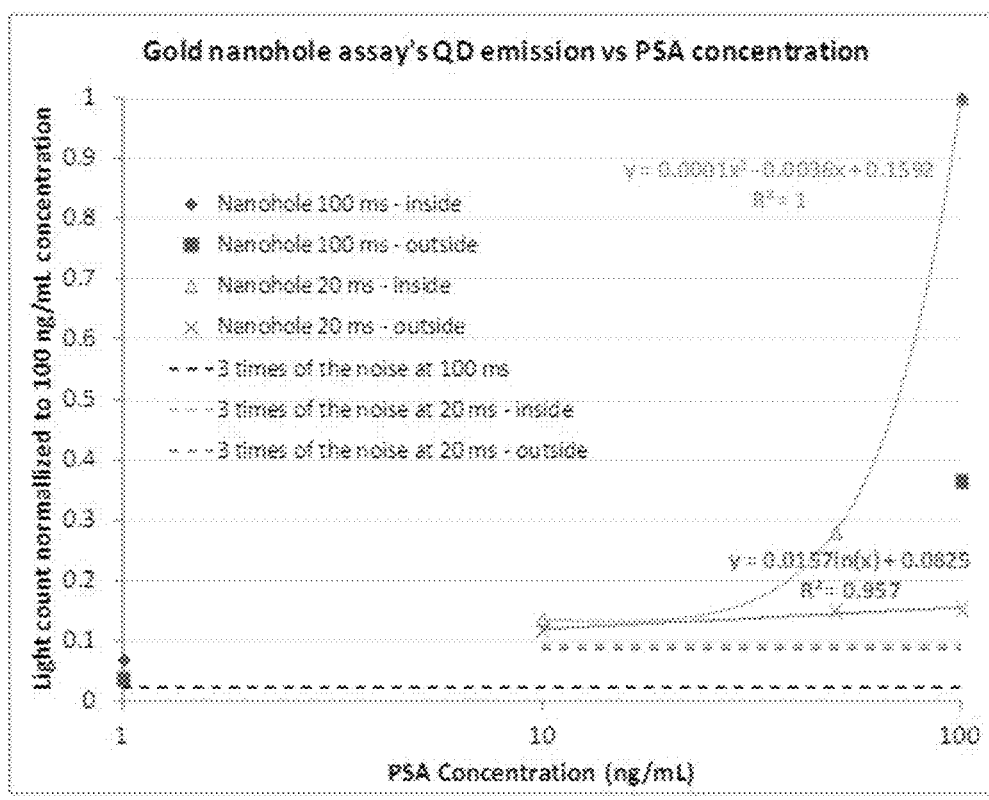
FIG. 10 is a characterization curve of quantum dot bioassay for PSA detections with gold nanohole chips.
Figure 11A:
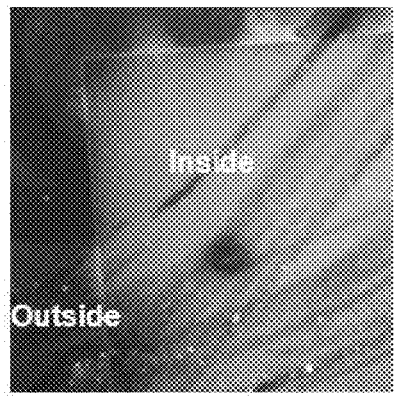
FIGS. 11A-11F show fluorescent images of quantum dots on gold nanopillar array at PSA concentrations of (a) 100 ng/ml (FIG. 11A), (b) control (FIG. 11B) (a gold nanopillar array chip but with no PSA added in the sandwich assay), (c) and (d) 50 ng/ml (FIGS. 11C and 11D), (e) 10 ng/ml (FIG. 11E) and (f) 5 ng/ml (FIG. 11F). The integration time was 100 ms.
Figure 11B:
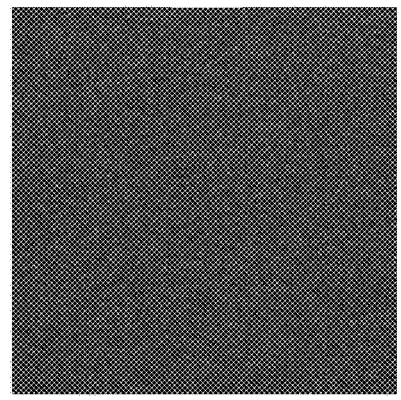
Figure 11C:
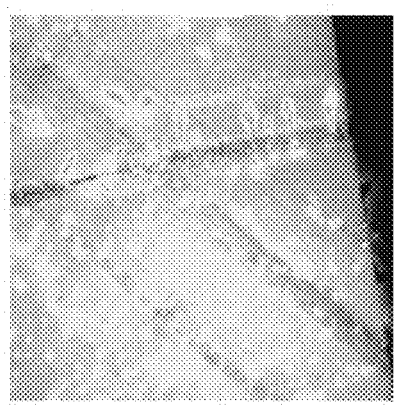
Figure 11D:
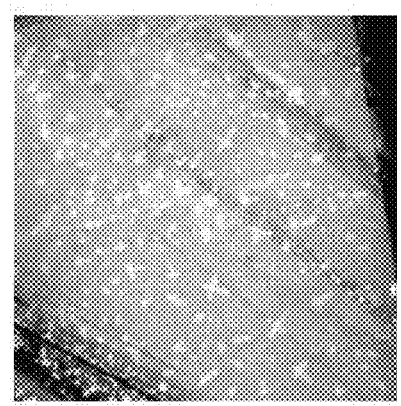
Figure 11E:
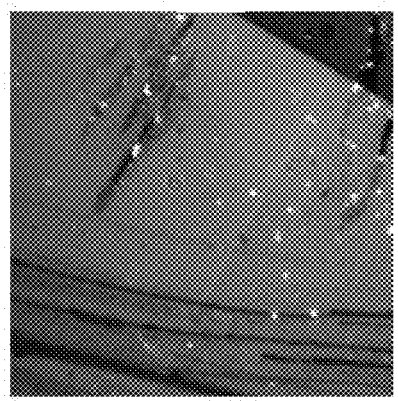
Figure 11F:
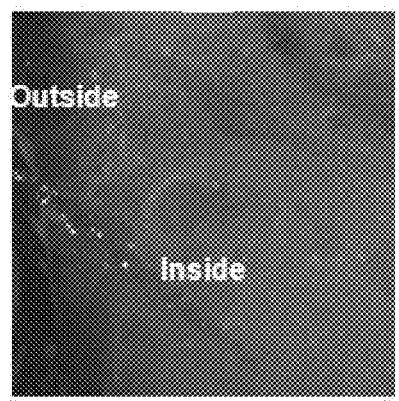

A summary of all quantum dot bioassay detections on the gold nanohole array chips are plotted in FIG. 10, with the quantum dot emission intensity normalized to the 100 ng/ml PSA QD emission for different integration time. In FIG. 10, at the fluorescence integration time of 20 ms, the response of the quantum dot emission on the gold nanoholes was nonlinear to the PSA concentration, i.e., the quantum dot signal decreased rapidly with the reduction of the PSA concentration. Outside the nanoholes on the gold film, the quantum dot emission was very low, but it was relatively linear to the PSA concentration. According to the fitted characterization curves of the PSA concentration and the 3 times of the noise line, it was very difficult to detect the PSA concentration of 1 ng/ml with 20 ms of integration. However, in FIG. 10, as the integration time increased to 100 ms, the noise count was about the same, the relative noise level normalized to the 100 pg/ml PSA quantum dot emission was 5 times smaller, therefore inside the nanohole, 1 ng/ml of PSA can be detected as shown in FIG. 7(c). Outside the nanohole, although the signal was slightly higher than the blank background noise in FIG. 7(c), because it was very close to the 3 times of noise level plotted in FIG. 10, it was difficult to detect 1 ng/ml of PSA on the gold film area.

Gold Nanopillar Array: As shown in the images in FIG. 11 integrated at 100 ms, the central nanopillar area demonstrated strong quantum dot fluorescence emission comparing to the outside glass substrate. Strong quantum dot signal was observed at 100 ng/ml of PSA. The quantum dot fluorescence with PSA as low as 5 ng/ml can be discerned by eyes under the Nikon CCD camera.

Figure 12A:
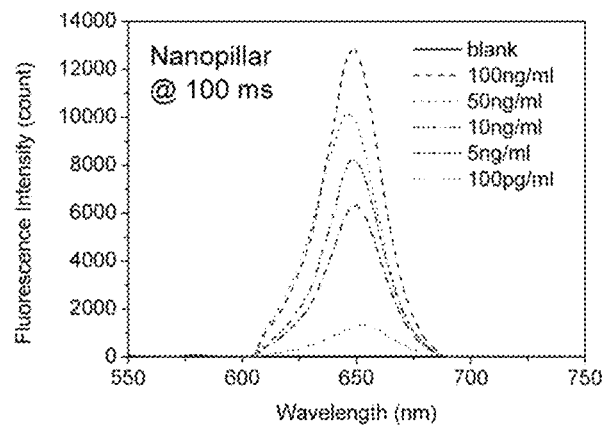
FIGS. 12A-12C show fluorescent spectra overlay of quantum dot bioassays for different PSA concentrations on gold nanopillar array, with the images taken at (a) 100 (FIG. 12A), (b) 50 (FIG. 12B), and (c) 20 ms (FIG. 12C).
Figure 12B:
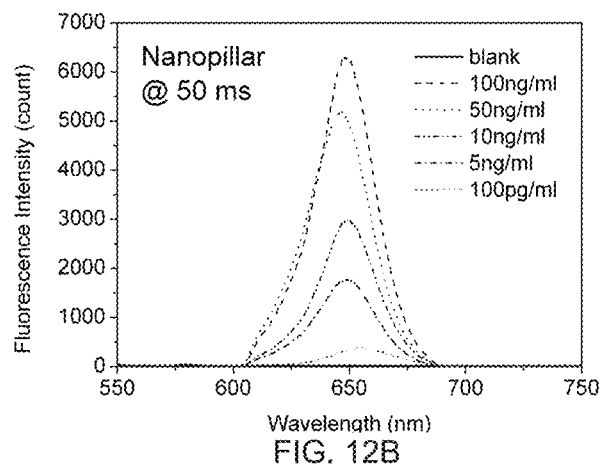
Figure 12C:
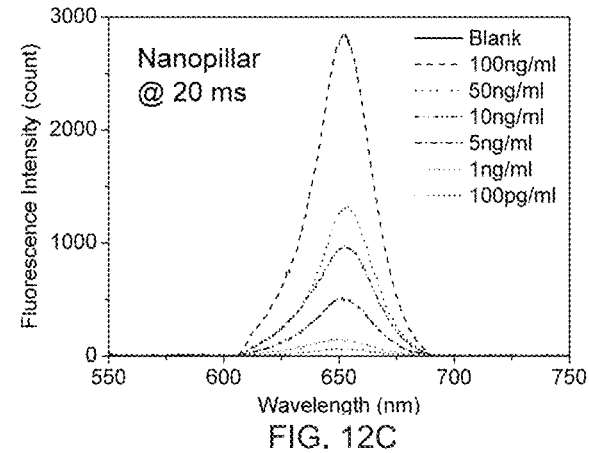

The overlay spectra of the quantum dot emissions on the gold nanopillars with different PSA concentrations at the integration time of (a) 100, (b) 50, and (c) 20 ms are plotted in FIG. 12. The fluorescence spectra are used to quantify the PSA concentration as low as 100 pg ml$^{-1}$, and the background noise was deducted by subtracting the minimum count in each spectrum. As shown in FIG. 12, PSA as low as 100 pg/ml was detectable at 20 ms exposure time.

Figure 13:
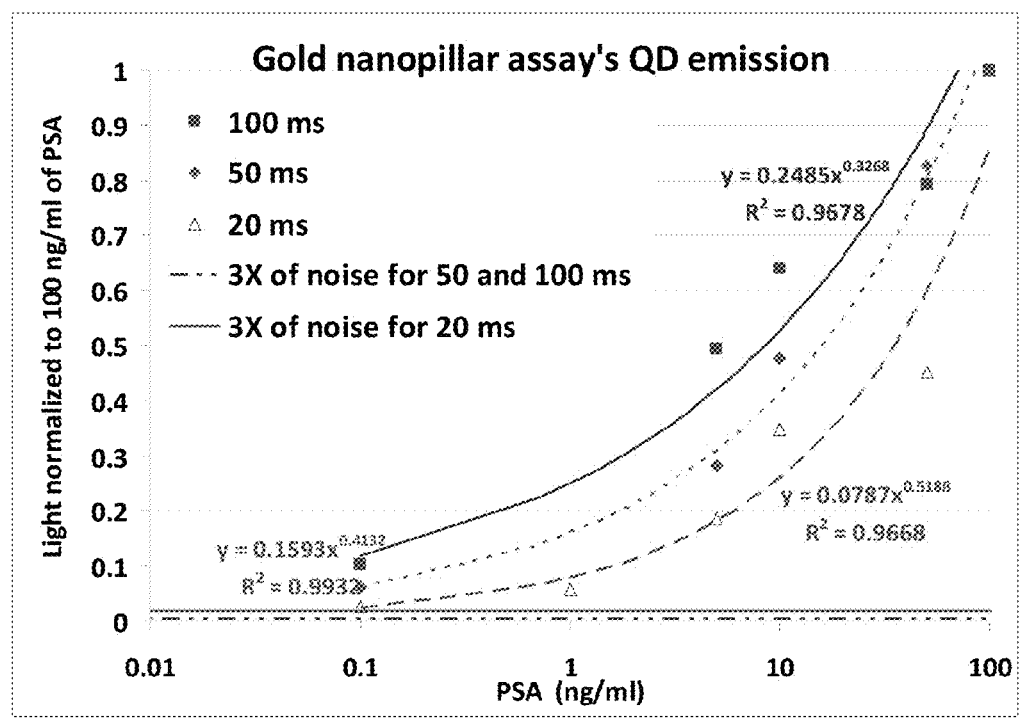
FIG. 13 is a characterization curve of quantum dot bioassay for PSA detections with gold nanopillar chips.

The characterization curves of the PSA detections are plotted in FIG. 13 with the count intensity normalized to 100 ng ml$^{-1}$. The curves indicate that for the gold nanopillars, PSA concentration of 100 pg ml$^{-1}$ can be detected at 20 ms of integration time at 3 times the noise level. However, based on a 3-time noise level, for 100 ms of integration time, the LOD of the sandwich PSA detection on the nanopillar chip will be less than 10 pg ml$^{-1}$. The QD emission curves at 50 and 100 ms are quasi-linear, while it is highly nonlinear at 20 ms at a high concentration. This is because the longer integration time suppresses the noise and enhances the weak signal. Since the QD bioassay is still quasi-linear after 100 ms, it seems even a longer integration time can further increase the detection sensitivity and the curve's linearity. Other minor issues affecting the linearity of the QD bioassay might be the co-effect of the QD aggregation at a high PSA concentration (FIG. 5) and the tweezers effect of the plasmonic field. Due to the tweezers effect, the plasmonic field will attract the QD sandwich bioassay into the plasmonic area; however, it takes some time. Since the QDs are already piled up tightly at the high PSA concentration, the tweezers effect should be more obvious for lower PSA concentrations and longer integration times such as 100 ms. Assuming the QD emission spectra are in Gaussian distribution in FIG. 12(a) and FIG. 12(c), 100, 50, 10, 5, and 0.1 ng m$^{-1}$ of PSA concentrations have $1.53 \times 10^6$, $1.40 \times 10^6$, $1.30 \times 10^6$, $121 \times 10^6$ and $9.55 \times 10^5$ counts per second for each spectrum, respectively. $1.53 \times 10^6$ cps is considered to be a high fluorescent intensity, which is the reason for the QD images to be directly observed with the naked eye under a dark-field microscope.

The linear intensity of the QD emission is related with the brightness of the images in FIG. 11, based on the count differences for the QD emission peaks at different PSA concentrations, the linear light intensities for 50, 10, 5 and 0.1 ng ml$^{-1}$ of PSA are 0.71, 0.55, 0.43 and 0.22 of the intensity for 100 ng ml$^{-1}$ of PSA. This estimation is very close to the image intensity difference shown in FIG. 11 for these PSA concentrations. Although the correlations between the images and fluorescence spectra greatly helped to analyze the QD bioassay's emissions, in real applications of the QD bioassay, it can be detected by a conventional optical detector for QD signal quantifications, as the QD emission is as strong as one million counts per second.

Example 4

Surface and Volume Coverage of the Quantum Dots

The gold nanopillar array performed better than the gold nanohole array with a much more linear PSA detection curve, higher sensitivity and lower noise level, because at the wavelength of 540 nm, the calculated plasmonic field intensity for the gold nanopillars was about 20-25% higher than that for the gold nanoholes.

Furthermore, the gold nanopillars also had a much higher surface and volume coverage of the QDs enhanced by the plasmonic field than the gold nanoholes. Based on the simulations of plasmonic field in FIG. 4(b) and FIG. 4(d), the quenching effect, and the geometry of our designed gold nanoholes and nanopillars, we can assume that only the QDs within a lateral distance of 15 nm to the rims and within a vertical distance of 5-15 nm to the gold surface were effectively excited by plasmon. Thus the surface coverage (ratio of the surface area of the QDs to the gold nanostructure area) of the QDs that can be excited by plasmons is about 18% for square gold nanoholes and 66% for gold nanopillars, while the volume coverage (ratio of the volume of QDs to the gold nanostructure volume) is about 4.8% for the square gold nanoholes, and 40% for the gold nanopillars. As the AFM images in FIG. 5 and FIG. 6 show that gold nanoholes have more QDs on the surface than the nanopillars, this infers that it is the QDs excited by the plasmons which determine the bioassay performance. Therefore, it is possible to further improve the QD bioassay's performance if the gold nanostructures are designed with the strongest plasmonic peak coincident with the QD excitation wavelength.

Hence, by choosing different shapes/types of the gold nanostructures, the sensitivity of the resultant bioassay can be tuned accordingly.

As seen from the above, the performance of the QD bioassay on the gold nanostructures may be affected by: (1) the plasmonic field intensity at the QD excitation wavelength; (2) the design of the bioassay such as controlling the distance between the nanostructures and the QDs, and controlling the orientation of the PSA capturing links via cleft antibody fragments; (3) the number of QDs being excited by the plasmons; and (4) the optical integration time. Here, the PSA are detected at 100 pg ml$^{-1}$ and 1 ng ml$^{-1}$ on gold nanopillar and nanohole arrays, respectively, for 100 ms of optical integration time. The LOD of the PSA detection is less than 10 pg ml$^{-1}$ on the Nikon Ti Eclipse microscope due to the low noise of its camera. The detection sensitivity can be improved by tuning the plasmonic peak with dimension optimized gold nanostructures.

INDUSTRIAL APPLICABILITY

The method or kit of the present disclosure may be employed in a bioassay which can be used in medical, healthcare and research industries. Due to the ease of detecting the fluorescence emitted by the quantum dots, simple and relatively inexpensive detectors can be used. In addition, due to the high sensitivity of the bioassay, the bioassay may be used to detect target analytes that are present in a body sample in a concentration as low as 100 pg/ml.

The method or kit of the present disclosure may be suitable for either highly sensitive analyte detections on standard optical detection equipment, or for a miniaturized optical point-of-care system where the detection sensitivity of optical components is relatively low.

The method or kit of the present disclosure may not require the use of complicated configuration or system (such as for example the Kretschmann configuration). The method or kit of the present disclosure also may not require the use of expensive or inconvenient devices such as a dark-field condenser or high quality optical filter to reduce background noise in order to read the fluorescence emission.

The bioassay may be used for detecting biomarkers with relatively low molecular weight, due to the big size and brightness of the inorganic fluorescent particles (quantum dots) with effective plasmonic amplification. Furthermore, the large Stokes shift of the inorganic fluorescent particles (quantum dots) facilitates the easy separation and detection of the weak emission at low antigen concentration from the strong excitation light. The bioassay may be incorporated with microfluidics to form a point-of-care system, which can use a laser beam as a light source and a microscope camera as its detector, without sacrificing much of the clinical required detection sensitivity.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

All referenced publications, patents and patent documents are incorporated by reference herein, as though individually incorporated by reference.

What is claimed is:

1. A method for detecting the presence or absence of a target analyte in a sample based on a localized surface plasmon resonance using a kit consisting of:
   a substrate having a plurality of nanostructures thereon;
   a capture biomolecule;
   a detection biomolecule;
   an inorganic fluorescent particle,
   an optional blocking agent; the method comprising the steps of:
   allowing said inorganic fluorescent particle to conjugate with said detection biomolecule that is bound specifically to said target analyte, if present in said sample, to form a detection reagent that emits a fluorescence, said target analyte additionally being specifically bound by said capture biomolecule immobilized on or within the plurality of nanostructures; and detecting the fluorescence emitted by said detection reagent, upon excitation by a light source, said plurality of nanostructures generating a localized surface plasmon resonance effect when the distance between said plurality of nanostructures and said inorganic fluorescent particle is within 5 to 15 nm to thereby enhance the fluorescence emitted by said detection reagent when bound to the target analyte, wherein the detected fluorescence indicates the presence of said target analyte in said sample, wherein a fluorescent emission signal is detected by an optical detector or a camera; and wherein the kit does not use the Kretschmann configuration.

2. The method of claim 1, wherein said plurality of nanostructures includes nanoholes, nanopillars or gratings.

3. The method of claim 1, wherein said plurality of nanostructures comprises a metal selected from the group consisting of aluminum, cobalt, copper, gold, indium, molybdenum, nickel, palladium, platinum, silver, tin, titanium, tungsten, zinc, alloys and combinations thereof.

4. The method of claim 1, wherein said detection biomolecule is an antibody, protein, nucleic acid, antibody fragment, a peptide or an oligonucleotide.

5. The method of claim 1, further comprising, before said allowing step, the steps of providing a sample suspected of containing said target analyte to said immobilized capture biomolecule and allowing said target analyte to bind to said immobilized capture biomolecule.

6. The method of claim 5, further comprising, before said providing and allowing steps, the step of immobilizing said capture biomolecule on or within said plurality of nanostructures.

7. The method of claim 1, wherein said inorganic fluorescent particle is a semiconductor nanocrystal.

8. The method of claim 7, wherein said semiconductor nanocrystal is a quantum dot selected from the group consisting of CdO, CdS, CdSe, CdTe, CdSeTe, CdHgTe, ZnS, ZnSe, ZnTe, ZnO, MgTe, MgS, MgSe, MgO. GaAs, GaP, GaSb, GaN, HgO, HgS, HgSe, HgTe, CaS, CaSe, CaTe, CaO, SrS, SrSe, SrTe, SrO, BaS, BaSe, BaTe, BaO, InAs, InP, InSb, InN, AlAs, AlN, AlP, AlSb, AlS, PbO, PbS, PbSe, PdTe, Ge, Si, ZnO, ZnS, ZnSe, ZnTe and combinations thereof.

9. The method of claim 1, wherein said capture biomolecule is an antibody, protein, nucleic acid, antibody fragment, a peptide or an oligonucleotide.

10. The method of claim 9, wherein said antibody fragment is selected from the group consisting of a F(ab')$_2$, Fab, Fab', Fd, Fv dAb, camelid antibody fragments, nanobody, isolated complementarity determining region, sFv, scFv and recombinant IgG fragment.

11. The method of claim 9, wherein said antibody fragment, peptide or oligonucleotide is functionalized with a chemical moiety for binding to said nanostructure.

12. A kit for detecting the presence or absence of a target analyte in a sample based on a localized surface plasmon resonance, wherein the kit consists of:
a substrate having a plurality of nanostructures thereon;
a capture biomolecule;
a detection biomolecule;
an inorganic fluorescent particle; and
an optional blocking agent,
wherein the capture biomolecule is immobilized on or within the plurality of nanostructures;
wherein the capture biomolecule binds specifically to the target analyte, if said target analyte is present in said sample;
wherein the detection biomolecule binds specifically to the target analyte, if said target analyte is present in said sample;
wherein the inorganic fluorescent particle is conjugated with said detection biomolecule to form a detection reagent that emits a fluorescence,
wherein upon excitation of a light source, said plurality of nanostructures generates a localized surface plasmon resonance effect when the distance between said plurality of nanostructures and said inorganic fluorescent particle is within 5 to 15 nm to thereby enhance the fluorescence emitted by said detection reagent when bound to the target analyte,
wherein a fluorescent emission signal is detected by an optical detector or a camera,
wherein the kit does not use the Kretschmann configuration.

13. The kit of claim 12, wherein said plurality of nanostructures includes nanoholes, nanopillars or gratings.

14. The kit of claim 12, wherein said plurality of nanostructures comprises a metal selected from the group consisting of aluminum, cobalt, copper, gold, indium, molybdenum, nickel, palladium, platinum, silver, tin, titanium, tungsten, zinc, alloys and combinations thereof.

15. The kit of claim 12, wherein said detection biomolecule is an antibody, protein, nucleic acid, functional antibody fragment, a peptide or an oligonucleotide.

16. The kit of claim 12, wherein said inorganic fluorescent particle is a semiconductor nanocrystal.

17. The kit of claim 16, wherein said semiconductor nanocrystal is a quantum dot selected from the group consisting of CdO, CdS, CdSe, CdTe, CdSeTe, CdHgTe, ZnS, ZnSe, ZnTe, ZnO, MgTe, MgS, MgSe, MgO, GaAs, GaP, GaSb, GaN, HgO, HgS, HgSe, HgTe, CaS, CaSe, CaTe, CaO, SrS, SrSe, SrTe, SrO, BaS, BaSe, BaTe, BaO, InAs, InP, InSb, InN, AlAs, AlN, AlP, AlSb, AlS, PbO, PbS, PbSe, PdTe, Ge, Si, ZnO, ZnS, ZnSe, ZnTe and combinations thereof.

18. The kit of claim 12, wherein said capture biomolecule is an antibody, protein, nucleic acid, functional antibody fragment, a peptide or an oligonucleotide.

19. The kit of claim 18, wherein said antibody fragment is selected from the group consisting of a F(ab')$_2$, Fab, Fab', Fd, Fv dAb, camelid antibody fragments, nanobody, isolated complementarity determining region, sFv, scFv and recombinant IgG fragment.

20. The kit of claim 18, wherein said antibody fragment, peptide or oligonucleotide is functionalized with a chemical moiety for binding to said nanostructure.

* * * * *